United States Patent
Kajihara et al.

(10) Patent No.: US 9,073,978 B2
(45) Date of Patent: Jul. 7, 2015

(54) METHOD FOR PRODUCING GLYCOPEPTIDE HAVING SIALYL SUGAR CHAIN, SIALYL SUGAR CHAIN-ADDED AMINO ACID DERIVATIVE TO BE USED IN SAME, AND GLYCOPEPTIDE

(75) Inventors: Yasuhiro Kajihara, Osaka (JP); Masumi Murakami, Osaka (JP); Kazuyuki Ishii, Kyoto (JP)

(73) Assignee: Glytech, Inc., Shimogyo-ku, Kyoto-shi, Kyoto (JP)

( * ) Notice: Subject to any disclaimer, the term of this patent is extended or adjusted under 35 U.S.C. 154(b) by 0 days.

(21) Appl. No.: 14/004,122

(22) PCT Filed: Mar. 5, 2012

(86) PCT No.: PCT/JP2012/055543
§ 371 (c)(1),
(2), (4) Date: Nov. 6, 2013

(87) PCT Pub. No.: WO2012/121206
PCT Pub. Date: Sep. 13, 2012

(65) Prior Publication Data
US 2014/0058062 A1    Feb. 27, 2014

(30) Foreign Application Priority Data

Mar. 10, 2011  (JP) .................................. 2011-053644
Feb. 2, 2012   (JP) .................................. 2012-021367

(51) Int. Cl.
*C07H 1/00* (2006.01)
*C07K 1/06* (2006.01)
(Continued)

(52) U.S. Cl.
CPC .............. *C07K 14/001* (2013.01); *C07K 1/068* (2013.01); *C07H 1/00* (2013.01); *C07K 1/006* (2013.01)

(58) Field of Classification Search
None
See application file for complete search history.

(56) References Cited

U.S. PATENT DOCUMENTS

2004/0181054 A1   9/2004  Kajihara et al.
2005/0222382 A1   10/2005  Kajihara
(Continued)

FOREIGN PATENT DOCUMENTS

EP    1 520 858 A1    4/2005
EP    1 650 226 A1    4/2006
(Continued)

OTHER PUBLICATIONS

Murakami et al. Chemical Synthesis of an Erythropoietin Glycoform Containing a Complex-type Disialyloligosaccharide. Angewandte Chemie, International Edition. Feb. 3, 2012, vol. 51, pp. 3567-3572.*
(Continued)

*Primary Examiner* — Jeffrey E Russel
(74) *Attorney, Agent, or Firm* — Myers Bigel Sibley & Sajovec, P.A.

(57) ABSTRACT

[Technical Problem]
To provide a method for manufacturing that enables to obtain a targeted glycopeptide harboring a sialyl sugar chain in high yield without decomposing sialic acid at a non-reducing terminal of sugar chain when the glycopeptide is synthesized by a Boc solid phase synthesis method.
[Solution to Problem]
The present invention is characterized in that the Boc-sialylglycosylated amino acid derivative used in Boc solid phase synthesis method is one where the carboxyl group of the sialic acid at the sugar chain non-reducing terminal is protected with a phenacyl group.

16 Claims, 7 Drawing Sheets

(51) Int. Cl.
*C07K 14/00* (2006.01)
*C07K 1/00* (2006.01)

(56) References Cited

U.S. PATENT DOCUMENTS

2007/0060543 A1 3/2007 Kajihara et al.
2012/0114595 A1 5/2012 Kajihara et al.

FOREIGN PATENT DOCUMENTS

| WO | WO 96/34878 A1 | 11/1996 |
| WO | WO 03/008431 A1 | 1/2003 |
| WO | WO 2004/005330 A1 | 1/2004 |
| WO | WO2004/007661 A2 | 1/2004 |
| WO | WO 2005/010053 A1 | 2/2005 |
| WO | WO 2011/007747 A1 | 1/2011 |

OTHER PUBLICATIONS

Hutloff A. et al. "ICOS is an inducible T-cell co-stimulator structurally and functionally related to CD28", *Nature*, 397:263-266, Jan. 21, 1999.

Xianzhang Bu et al. "An improved deblocking agent for direct Fmoc solid-phase synthesis of peptide thiosesters", *Tetrahedron Letters*, 43, 2419-2422, 2002.

European Search Report Corresponding to European Patent Application No. EP12755521; Dated: Aug. 20, 2014; 7 Pages.

Yasuhiro Kajihara et al:"Synthesis of diverse asparagine linked oligosaccharides and synthesis of sialylglycopeptide on solid phase" *Current Medicinal Chemistry*, vol. 12, No. 5, Jan. 1, 2005, pp. 527-550.

* cited by examiner

METHOD FOR PRODUCING GLYCOPEPTIDE HAVING SIALYL SUGAR CHAIN, SIALYL SUGAR CHAIN-ADDED AMINO ACID DERIVATIVE TO BE USED IN SAME, AND GLYCOPEPTIDE

STATEMENT OF PRIORITY

This application is a 35 U.S.C. §371 national phase application of International Application Serial No. PCT/JP2012/055543, filed Mar. 5, 2012, which claims the benefit, under 35 U.S.C. §119 (a), of Japanese Patent Application Nos. 2011-053644, filed Mar. 10, 2011, and 2012-021367, filed Feb. 2, 2012, the entire contents of each of which are incorporated by reference herein.

STATEMENT REGARDING ELECTRONIC FILING OF A SEQUENCE LISTING

A Sequence Listing in ASCII text format, submitted under 37 C.F.R. §1.821, entitled 9778-7TSST25.txt, 25,236 bytes in size, generated on Mar. 24, 2015 and filed via EFS-Web, is provided in lieu of a paper copy. This Sequence Listing is hereby incorporated by reference into the specification for its disclosures.

TECHNICAL FIELD

The present invention relates to a method for synthesizing a glycopeptide having a sialyl sugar chain that may be applied to e.g. reference standards such as for pharmaceutical agents or analytical instruments and reagents for academic purposes.

BACKGROUND ART

In recent years, glycomolecules have been gathering attention as the third chain-like biological molecule following nucleic acids (DNA) and proteins. The human body is one great big cellular society consisting of about 60 trillion cells, and all cell surfaces are covered with glycomolecules. For example, the ABO blood group system is determined by the difference of sugar chains on the cell surface.

Sugar chains have a function related to intercellular recognition and interaction, acting as a keystone in constituting the cellular society. Derangement in the cellular society will lead to e.g. cancer, chronic disease, infection, and aging. For example, it is known that structural change of sugar chains on the cell surface occurs when a cell becomes cancerous.

In addition, it is known that *Vibrio cholerae* or influenza virus etc. invade the cell and cause infection by recognizing and binding to a particular sugar chain.

The elucidation of such sugar chain functions leads to, e.g. the development of pharmaceutical agents or foods based on a new principle, and broad applications such as prevention of illnesses and contribution to therapies are expected.

Sugar chains have very complex structures compared to nucleic acid or protein structures due to diversities such as monosaccharide sequence, binding mode and site, chain length and branching mode, and general higher-order structure. Accordingly, the biological information derived from the structure of sugar chain is widely varied compared to that from nucleic acids or proteins. Although the importance of sugar chain research is acknowledged, the propulsion of research is in a delayed state compared to nucleic acids or proteins due to the complexity and diversity of the structure of sugar chain.

Many of the proteins present on the cell membrane surface or in the serum etc. have a sugar chain bound thereto. A molecule where a sugar chain is covalently bound to a protein is called a glycoprotein, and can be divided into two groups according to the difference in the binding mode of the sugar and the protein. One is the asparagine-linked sugar chain (N-glycosidic bond) where the amino group on the side chain of asparagine (Asn) is bound with the sugar chain. The other is the mucin-linked sugar chain (O-glycosidic bond) where the sugar chain is bound to the alcohol of serine (Ser) or threonine (Thr). All asparagine-linked sugar chains have a basic skeleton consisting of 5 sugar residues, and are classified into the subgroups of high mannose-type, complex-type, and hybrid-type according to the sugar residue type at the non-reducing terminal of the sugar chain bound. On the other hand, mucin-linked sugar chains are classified into four groups according to the difference in the basic skeleton (core).

Although proteins having a sugar chain have already been globally utilized as glycoprotein formulations, there were problems that these glycoproteins could only be obtained by methods mainly utilizing biotechnology, and that glycoproteins manufactured thereby were low in purity. Accordingly, a chemical synthesis method that efficiently affords the glycoprotein of interest in high purity was desired. Specifically, when synthesizing a glycopeptide having a non-naturally occurring amino acid, biological methods are not capable of direct production.

The solid phase synthesis method developed by R. B. Merrifield in 1963 is currently widely used as a peptide synthesis method. The solid phase synthesis method is a method where amino acid building blocks are joined on a solid phase called a resin and the peptide chain is elongated. When the peptide chain elongation is complete, the peptide chain is cleaved from the solid phase to afford the target object.

As an application of this, an amino acid bound to a sugar chain can be integrated upon peptide chain elongation to enable glycopeptide chain synthesis.

In the solid phase synthesis method, the amino group of the amino acids to be the building blocks is protected by e.g. a fluorenylmethoxycarbonyl (Fmoc) group, a tert-butoxycarbonyl (Boc) group, or a benzyloxycarbonyl (Cbz or Z).

In the solid phase synthesis method employing a Boc group, a super strong acid such as hydrogen fluoride is used for deprotecting the protecting group of the peptide side chain and cleaving out the peptide itself from the resin, and there was a problem that when a sugar chain is contained in a portion of the target object due to this hydrogen fluoride treatment, the sugar chain portion, especially the sialic acid present at the sugar chain non-reducing terminal is easily degraded. It was thus difficult to directly manufacture the glycoprotein of interest having a sialyl sugar chain with Boc solid phase synthesis method.

In the solid phase synthesis method employing an Fmoc group, the Fmoc group can be detached from the amino group of an amino acid under basic condition. On the other hand, since the Boc group can be deprotected from the amino group of an amino acid under acidic condition, Boc solid phase synthesis method is necessary when synthesizing a peptide or a glycopeptide employing a base-labile non-naturally occurring amino acid with solid phase synthesis method.

Non-naturally occurring amino acids are amino acids that do not configure proteins but some exists in nature, and can also be obtained by chemical synthesis. Non-naturally occurring amino acids have extremely high diversity of structure or flexibility of substituent selection. Improvement of in vivo stability, improvement of potency, improvement of absorption efficiency, improvement of distribution within tissue, and change of three-dimensional structure of peptide etc. can be expected by utilizing such a non-naturally occurring amino acid to synthesize a peptide, and non-naturally occurring amino acids are gathering attention as allowing designing of candidate substances for novel peptide medicines and functional materials.

As one solid phase synthesis method, there is also reported a method wherein the peptide produced when cleaving the peptide off from the resin is converted into a thioester form (e.g. Non-Patent Literature 1). Once a peptide in thioester form is obtained, it can be bound to other peptide chains by utilizing e.g. Native Chemical Ligation (NCL method) or Kinetically Controlled Ligation (KCL method), allowing a larger protein of interest to be manufactured (Patent Literature 1 and Non-Patent Literature 2).

The NCL method is a method of obtaining a larger peptide chain by linking a peptide fragment having Cys at the N-terminal amino acid and a peptide fragment having a thioester at the C-terminal. A glycoprotein can be synthesized by employing a glycosylated peptide fragment for this. Each fragment can be synthesized by for example the above solid phase synthesis method, and glycosylated fragments having uniform amino acid sequence and sugar chain structure can be obtained by binding a glycosylated asparagine having uniform sugar chains instead of an amino acid during synthesis (Patent Literature 2). In addition, the KCL method is a method of obtaining the glycoprotein of interest in relatively large amounts by utilizing the difference in reaction rate when both peptide fragments to be linked have a thioester at the C-terminal.

Accordingly, by performing the NCL or the KCL method with a glycosylated fragment, uniform glycoproteins that do not vary depending on the production lot and that can also be utilized as a pharmaceutical agent can be obtained.

CITATION LIST

Patent Literature

[Patent Literature 1] International Publication No. 96/30378
[Patent Literature 2] International Publication No. 2011/007747

Non-Patent Literature

[Non-Patent Literature 1] Xianzhang Bu. et al.: Tetrahedron Letters (2002) 43:2419-2422
[Non-Patent Literature 2] Hutloff A. et al.: Nature (1999) 397:263-266

SUMMARY OF INVENTION

Technical Problem

As described above, a synthesis method where it is possible to retain the sialic acid without being degraded from the sugar chain in Boc solid phase synthesis method is desired. The present inventors found a method of synthesizing a glycopeptide having a sialyl sugar chain by protecting the carboxyl group of the sialic acid on the sugar chain with a particular compound in solid phase synthesis method. However, under the super strong acid condition of Boc solid phase, synthesis method, the sialic acid at the sugar chain non-reducing terminal could not be sufficiently retained even when these protecting groups were used, and a glycopeptide having a sialyl sugar chain could not be obtained at a desired yield.

Accordingly, the present invention provides a method for synthesizing a glycopeptide having a sialyl sugar chain of interest at a high yield in a glycopeptide solid phase synthesis method employing a Boc group, without the sialic acid at the sugar chain non-reducing terminal being degraded.

Further, the present invention provides a method of manufacturing a glycopeptide in thioester form in a solid phase synthesis method of a glycopeptide having a sialyl sugar chain employing a Boc group.

Solution to Problem

As a result of extensive investigation by the present inventors to solve the above problems, it became possible to considerably improve the yield of a glycopeptide having a sialyl sugar chain even in Boc solid phase synthesis method by using a phenacyl group as the protecting group of the carboxyl group of the sialic acid at the sugar chain non-reducing terminal.

In other words, the present invention relates to a method for manufacturing a glycopeptide having a sialyl sugar chain, characterized in that it comprises the following steps of:

(1) binding a resin having a hydroxyl group with an amino acid having the amino group nitrogen protected with a Boc group; wherein said binding step is a step of binding the hydroxyl group of said resin with the carboxyl group of said amino acid by an esterification reaction, (2) forming a free amino group by detaching said Boc group;

(3) repeating at least once the following steps (i) and (ii) of:
  (i) elongating the amino acid bound to the resin by further binding another amino acid having the amino group nitrogen protected with a Boc group,
wherein said elongation step is a step of binding the carboxyl group of said another amino acid with said free amino group of the amino acid bound to said resin,
  (ii) forming a free amino group by detaching said Boc group in (i); and (4) cleaving the resin with an acid;
wherein said amino acid in step (1) and/or said another amino acid in at least once of (i) in step (3) is a glycosylated amino acid, said glycosylated amino acid has a sialic acid at at least one of the sugar chain non-reducing terminals, and the carboxyl group of said sialic acid is protected with a phenacyl group.

One embodiment of the method of the present invention for manufacturing a glycopeptide having a sialyl sugar chain is characterized in that said glycosylated amino acid is an asparagine-linked sugar chain or a mucin-type linked sugar chain.

Further, one embodiment of the method of the present invention for manufacturing a glycopeptide having a sialyl sugar chain is characterized in that said acid in said step (4) is a mixed acid of trifluoroacetic acid/trifluoromethanesulfonic acid/dimethyl sulfide/m-cresol.

Further, one embodiment of the method of the present invention for manufacturing a glycopeptide having a sialyl sugar chain is characterized in that said amino acid in said step (1) and/or said another amino acid in at least once of (i) in said step (3) is a base-labile non-naturally occurring amino acid.

Further, one embodiment of the method of the present invention for manufacturing a glycopeptide having a sialyl sugar chain is characterized in that at least one of said glycosylated amino acids is sialylglycoasparagine, and said sialylglycoasparagine has 6 or more sugar residues.

Further, one embodiment of the method of the present invention for manufacturing a glycopeptide having a sialyl sugar chain is characterized in that at least one of said glycosylated amino acids is sialylglycoasparagine, and said sialylglycoasparagine has 9 to 11 sugar residues.

Further, one embodiment of the method of the present invention for manufacturing a glycopeptide having a sialyl sugar chain is characterized in that at least one of said glycosylated amino acids is sialylglycoasparagine, and said glycoasparagine has 6 or more sugar residues and has a biantennary sugar chain bound thereto.

Further, one embodiment of the method of the present invention for manufacturing a glycopeptide having a sialyl sugar chain is characterized in that said glycosylated amino acid is represented by Formula (1):

[Chemical Formula 1]

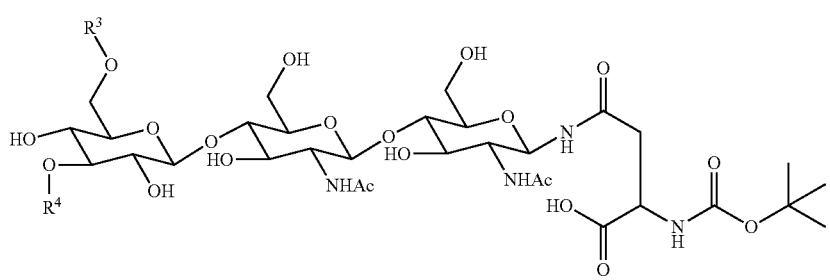

(1)

[wherein one of $R^3$ and $R^4$ is (2), and the other is a group selected from the group consisting of a hydrogen atom and groups shown in Formulae (2) to (6).]

[Chemical Formula 2]

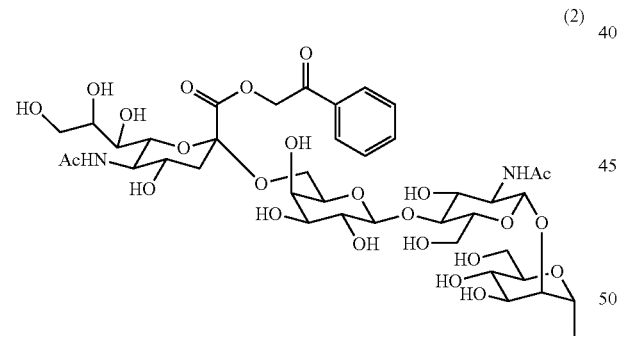

(2)

[Chemical Formula 3]

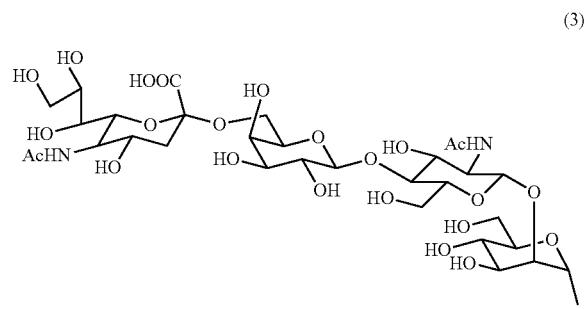

(3)

[Chemical Formula 4]

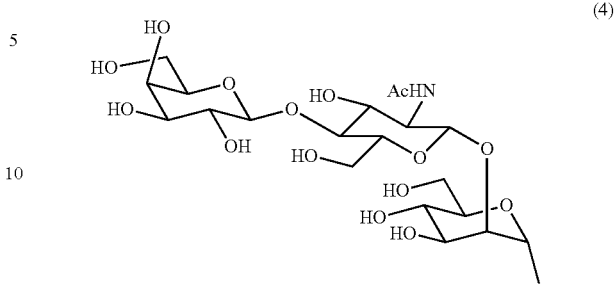

(4)

[Chemical Formula 5]

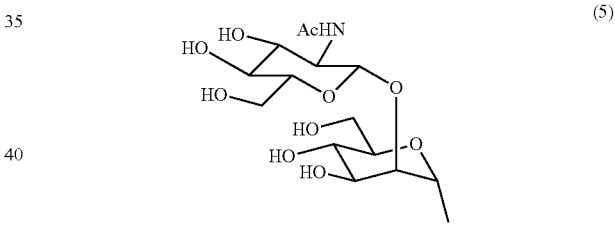

(5)

[Chemical Formula 6]

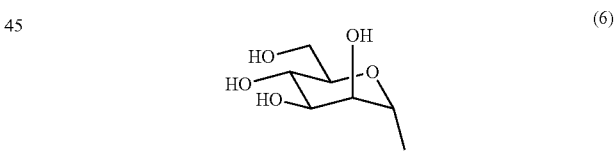

(6)

Further, one embodiment of the method of the present invention for manufacturing a glycopeptide having a sialyl sugar chain is characterized by further comprising a step of binding a thiol compound to the resin before said step (1).

Further, one embodiment of the method of the present invention for manufacturing a glycopeptide having a sialyl sugar chain is characterized by further comprising a step of (5) linking a thioester form of a glycopeptide having a sialyl sugar chain with a peptide fragment or a glycopeptide fragment.

Further, one embodiment of the method of the present invention for manufacturing a glycopeptide having a sialyl sugar chain is characterized by further comprising a step of allowing a labeling agent to react before the cleaving of the resin with the acid in said step (4).

Further, one embodiment of the method of the present invention for manufacturing a glycopeptide having a sialyl sugar chain is characterized in that the labeling agent is dansyl halide.

Further, one embodiment of the method of the present invention for manufacturing a glycopeptide having a sialyl sugar chain is characterized in that microwave irradiation is used for heating the condensation reaction of said amino acid and/or the detachment reaction of the Boc group in at least one of said steps (2) to (3).

Further, one embodiment of the method of the present invention for manufacturing a glycopeptide having a sialyl sugar chain is characterized by further comprising a step of deprotecting the phenacyl group protecting the carboxyl group of said sialic acid after said step (4).

Further, another aspect of the present invention relates to a glycopeptide having a sialyl sugar chain produced by the above manufacturing method.

Further, another aspect of the present invention relates to a method for manufacturing a sialylglycoasparagine derivative in which the amino group of sialylglycoasparagine is protected with a Boc group and the carboxyl group of the sialic acid at the sugar chain non-reducing terminal is protected with a phenacyl group, comprising the steps of: introducing a phenacyl group into a sialylglycoasparagine derivative having the amino group of the asparagine protected with a lipophilic protecting group, detaching the lipophilic protecting group of the sialylglycoasparagine having a phenacyl group introduced, and introducing a Boc group into the sialylglycoasparagine having the lipophilic protecting group detached.

Further, one embodiment of the method of the present invention for manufacturing a sialylglycoasparagine derivative is characterized in that said lipophilic protecting group is Fmoc.

Further, in one embodiment of the present invention, the glycopeptide manufactured by the method of the present invention for manufacturing a glycopeptide having a sialyl sugar chain is a glycopeptide having an amino acid sequence equivalent to the amino acid sequence of erythropoietin and having at least one or more sialyl sugar chains at any position. Further, in one embodiment of the present invention, the glycopeptide manufactured by the method of the present invention for manufacturing a glycopeptide having a sialyl sugar chain is a portion of glycopeptide (i.e., a glycopeptide fragment) having an amino acid sequence equivalent to the amino acid sequence of erythropoietin, and having at least one or more sialyl sugar chains at any position.

An amino acid sequence equivalent to the amino acid sequence of erythropoietin herein refers to an amino acid sequence that has erythropoietin function after folding and has deletion, substitution or addition of one or a few amino acids in the amino acid sequence of erythropoietin.

Advantageous Effects of Invention

According to the method of the present invention for manufacturing a glycopeptide having a sialyl sugar chain, a glycopeptide having a sialic acid at the sugar chain non-reducing terminal can be directly provided in the Boc solid phase synthesis method. Moreover, because a Boc group is employed as the protecting group for the amino group of an amino acid, it is also possible to produce a glycopeptide using a base-labile non-naturally occurring amino acid.

Glycopeptides having substantially uniform sugar chain structure can be synthesized in large amounts by chemical synthesis such as the Boc solid phase synthesis. Such a glycopeptide having uniform sugar chain structure is constant in quality, and is particularly preferred in fields such as manufacturing of pharmaceutical agents or assays.

DESCRIPTION OF EMBODIMENTS

Figure 1:
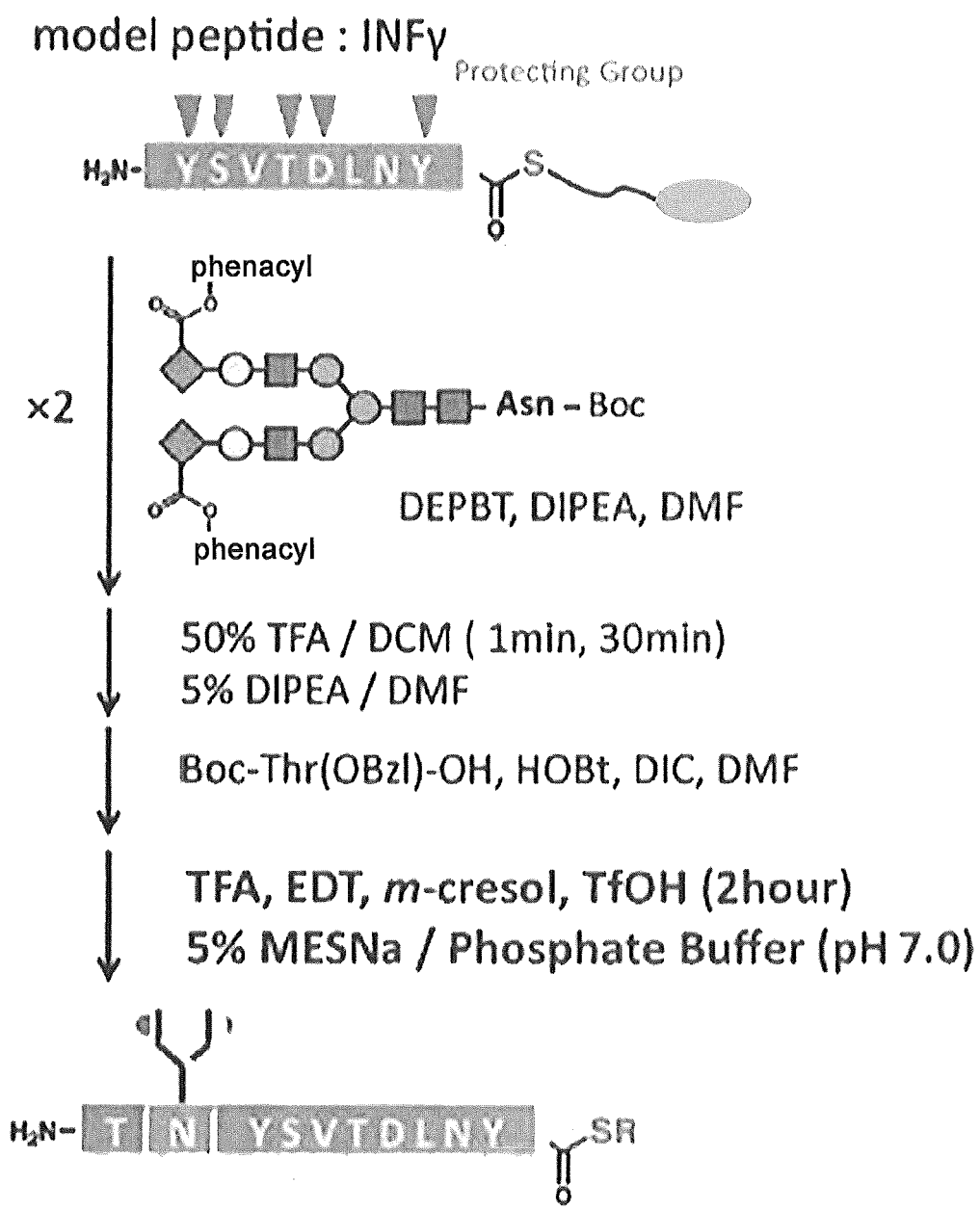
FIG. 1 is a schematic diagram showing the flow chart of an aspect of one embodiment of the present invention, which is the method for producing an amino acid sequence having a biantennary disialoglycoasparagine (TN(diphenacyl-disialo sugar chain)YSVTDLNY) (SEQ ID NO:1) by Boc solid phase synthesis method using interferon gamma (INFγ) as the model peptide (initial peptide, YSVTDLNY, comprises residues 3-10 of SEQ ID NO:1).
Figure 2:
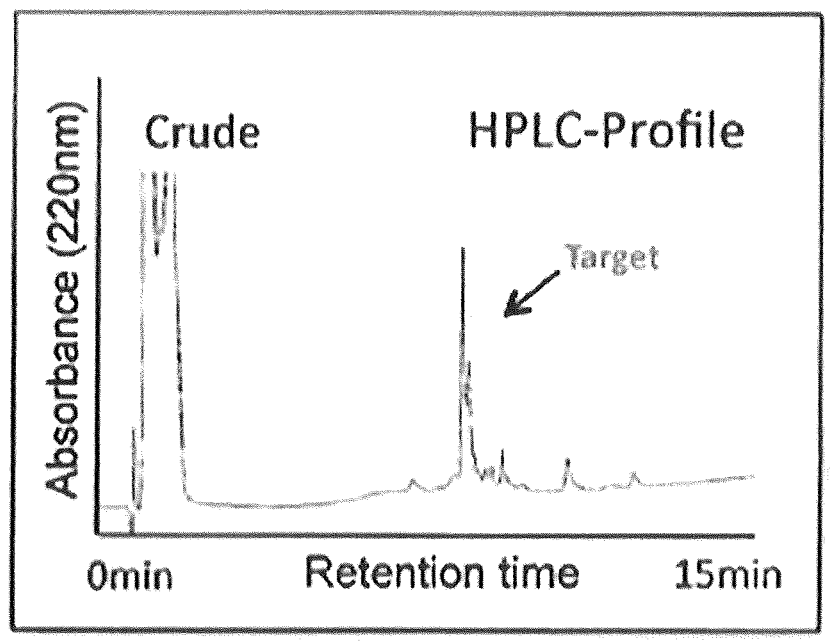
FIG. 2 shows the HPLC profile graph in an aspect of one embodiment of the present invention, which is the production of an amino acid sequence having a biantennary disialoglycoasparagine (TN(diphenacyl-disialo sugar chain)YSVT-DLNY) (SEQ ID NO:1) by Boc solid phase synthesis method using interferon gamma (INFγ) as the model peptide.
Figure 3:
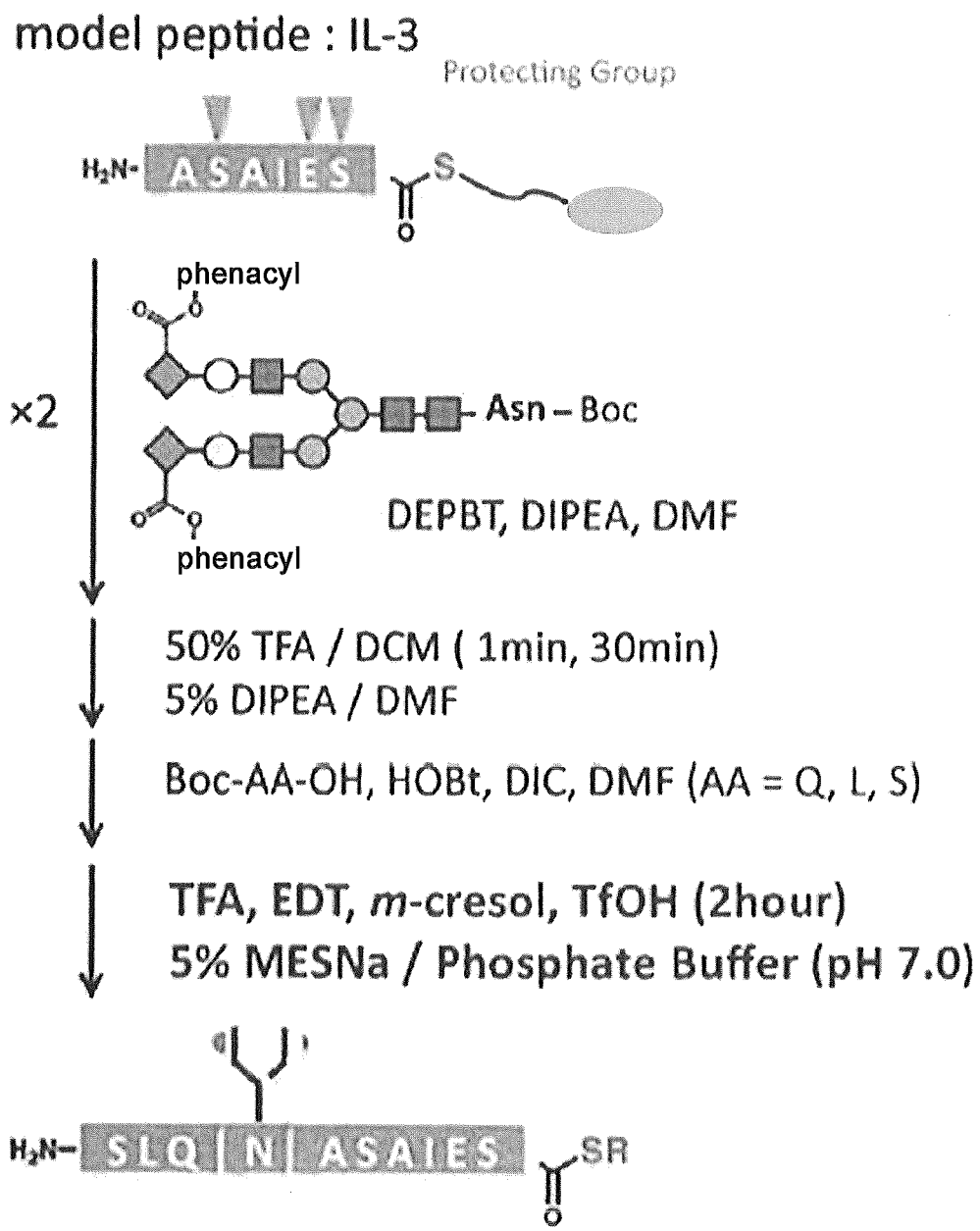
FIG. 3 is a schematic diagram showing the flow chart of an aspect of one embodiment of the present invention, which is the method for producing an amino acid sequence having a biantennary disialoglycoasparagine (SLQN(diphenacyl-disialo sugar chain)ASAIES) (SEQ ID NO:2) by Boc solid phase synthesis method using Interleukin 3 (IL-3) as the model peptide (initial peptide, ASAIES, comprises residues 6-10 of SEQ ID NO:2).
Figure 4:
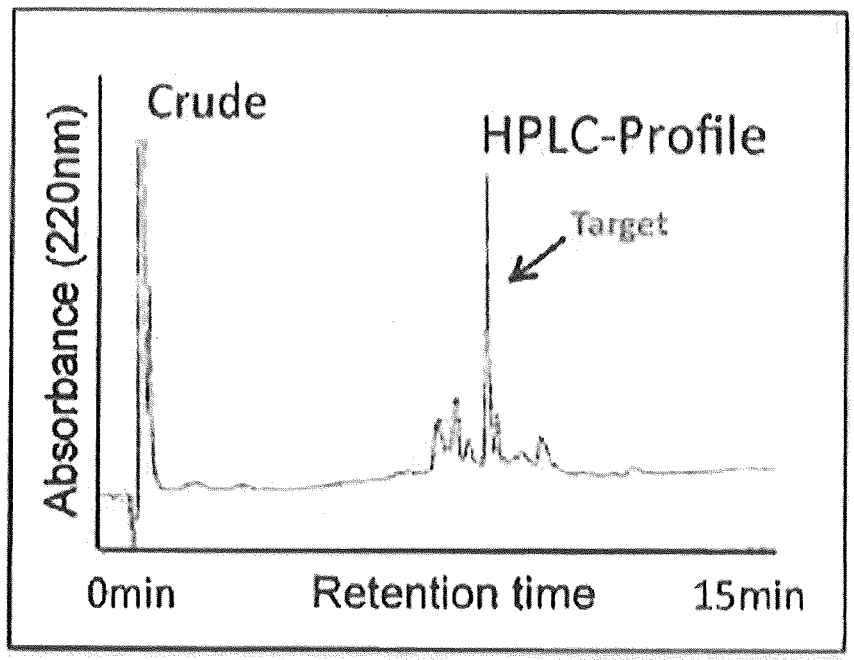
FIG. 4 shows the HPLC profile graph in an aspect of one embodiment of the present invention, which is the production of an amino acid sequence having a biantennary disialoglycoasparagine (SLQN(diphenacyl-disialo sugar chain) ASAIES) (SEQ ID NO:2) by Boc solid phase synthesis method using Interleukin 3 (IL-3) as the model peptide.

An "amino acid" herein is employed in the broadest meaning thereof, and comprises not only naturally-occurring amino acids but also non-naturally-occurring amino acids such as amino acid variants and derivatives. Those skilled in the art will take this broad definition into consideration to understand that examples of an amino acid herein include natural proteinogenic L-amino acids; D-amino acids; chemically modified amino acids such as amino acid variants and derivatives; natural non-proteinogenic amino acids such as norleucine, β-alanine, and ornithine; and chemically synthesized compounds having properties well-known in the art which are characteristic of amino acids. Examples of a non-natural amino acid herein include α-methylamino acids (such as α-methylalanine), D-amino acids, histidine-like amino acids (such as 2-amino-histidine, β-hydroxy-histidine, homohistidine, α-fluoromethyl-histidine and α-methyl-histidine), amino acids having extra methylene on the side chain ("homo" amino acids), and amino acids in which a carboxylic acid functional group in the side chain is substituted with a sulfonic acid group (such as cysteic acid). In a preferred aspect, the amino acid contained in the compound of the present invention comprises a non-naturally occurring amino acid.

A "sugar chain" herein refers to a compound made of one or more unit sugars (monosaccharide and/or a derivative thereof) in a row. When there are two or more unit sugars in a row, the bond between each unit sugar is a dehydration condensation by a glycoside bond. Examples of such a sugar chain include, but are not limited to, a wide variety such as monosaccharides and polysaccharides contained in vivo (glucose, galactose, mannose, fucose, xylose, N-acetylglucosamine, N-acetylgalactosamine, sialic acid, and complexes and derivatives thereof), as well as degraded polysaccharides, glycoproteins, proteoglycans, glycosaminoglycans, and sugar chains degraded or induced from complex biomolecules such as glycolipids. The sugar chain may be of linear or branched type.

A "sugar chain" herein also includes a sugar chain derivative, and examples of a sugar chain derivative include, but are not limited to, sugar chains wherein the sugar constituting the sugar chain is a sugar having a carboxyl group (e.g. aldonic acid where the C-1 position is oxidized to become a carboxylic acid (e.g. D-gluconic acid which is oxidized D-glucose) and uronic acid where the terminal C atom is made into a carboxylic acid (D-glucuronic acid which is oxidized D-glucose)), sugars having an amino group or an amino group derivative (e.g. acetylated amino group) (e.g. N-acetyl-D-glucosamine and N-acetyl-D-galactosamine), sugars having both an amino group and a carboxyl group (e.g. N-acetyl-neuraminic acid (sialic acid) and N-acetylmuramic deoxidized sugars (e.g. 2-deoxy-D-ribose), sulfated sugars comprising a sulfate group, and phosphorylated sugars comprising a phosphate group.

A sugar chain derivative herein also includes compounds where other compounds are bound to the reducing terminal of the sugar chain by dehydration condensation etc. An example can include a structure where a compound is further bound to N-acetylglucosamine at the reducing terminal of the sugar chain in an asparagine-linked sugar chain. A compound can be similarly added to the reducing terminal in case of other sugar chain derivatives as well.

Sugar chain derivatives include those where an amino acid is added to the reducing terminal of the sugar chain (glycosylated amino acid), as well as those where a peptide, a protein, a linker, a fluorescent group, a lipid, a low molecular compound, a radioactive compound, or the like is added. Amino acid comprises not only natural amino acids but also non-natural amino acids such as amino acid variants and derivatives. Amino acids, peptides, and proteins etc. may be those where a portion or all of the functional groups contained therein such as a hydroxyl group, an amino group, and a carboxyl group are protected with a protecting group. Examples of a protecting group for a hydroxyl group can include a methyl group, a benzyl group, a benzoyl group, an acetyl group, a trimethylsilyl (TMS) group, a triethylsilyl (TES) group, and a tert-butyldimethylsilyl (TBS or TBDMS) group. Examples of an amino protecting group can include, as a lipophilic protecting group, a carbonate-based or an amide-based protecting group such as 9-fluorenylmethoxycarbonyl (Fmoc) group, t-butyloxycarbonyl (Boc) group, a benzyl group, an allyloxycarbonyl group, and an acetyl group.

Preferred sugar chains herein are, with respect to the manufacture of glycoproteins to become pharmaceutical agents, sugar chains that exist in vivo as glycoconjugates (such as glycopeptides (or glycoproteins), proteoglycans, or glycolipids), preferably sugar chains that are bound in vivo to peptides (or proteins) as glycopeptides (or glycoproteins), such as N-linked sugar chains and O-linked sugar chains. An N-linked sugar chain is a generic term as a binding format when the sugar chain binds to a protein and refers to a sugar chain where the anomeric hydroxyl group in the N-acetylglucosamine at the reducing terminal of the sugar chain forms a dehydration condensation and binds with the amino group (—NH$_2$) of the asparagine side chain, and an O-linked sugar chain is a generic term as a binding format when the sugar chain binds to a protein and refers to a sugar chain where the anomeric hydroxyl group at the reducing terminal of the sugar chain forms a dehydration condensation and binds with the hydroxyl group (—OH) of serine or threonine side chain.

The N-linked sugar chain is also sometimes referred to as asparagine-linked sugar chain, glycoasparagine, or N-type sugar chain etc. The N-linked sugar chain is a sugar chain group having Man(β1-4)GlcNac(β1-4)GlcNac as the core of the basic skeleton. Moreover, multibranched-type structures such as biantennary, triantennary, and tetraantennary are also known as branched structures of sugar chain, and sugar chains having such branched structures are also included. These sugar chain structures are also described in e.g. Dictionary of Biochemistry (Seikagaku Jiten) (3rd Ed., Published by Tokyo Kagaku Dojin).

Further, a compound where Fuc (fucose) or Gn (N-acetylglucosamine) is bound to the above sugar chain is also known to exist as an N-linked complex-type sugar chain, and such a compound is also included. More specifically, it is known that Fuc forms an α1,6 bond to Gn at the reducing terminal, Gn forms a β1,4 bond to position 4 of Man bound to Gn at the reducing terminal, and Fuc forms an α1,3 or α1,4 bond to Gn in the branched portion. In addition, sugar chains having different binding modes of glycoside bond, such as a compound where the binding mode of the above sugar chain at the branched portion is Gn(β1,4)Man or Gn(β1,2)Man instead of Gn(β1,6)Man, or is Gn(β1,2)Man instead of Gn(β1,4)Man, a compound where a portion of Sia(α2,6)Gal at the sialic acid binding site is Sia(α2,3)Gal instead of Sia(α2,6)Gal, a compound where a portion of Sia(α2,3)Gal is Sia(α2,6)Gal instead of Sia(α2,3)Gal, are also included.

Gn or GlcNAc herein indicates N-acetylglucosamine, Man indicates mannose, and Gal indicates galactose.

A "glycosylated amino acid" herein refers to an amino acid having a sugar chain bound thereto, examples of which can include the N-linked and O-linked sugar chains described above. The sugar chain and the amino acid may be bound via a linker. There is no particular restriction on the binding site between the sugar chain and the amino acid, but it is preferred that the amino acid is bound to the reducing terminal of the sugar chain.

The type of amino acid that the sugar chain binds to is not particularly limited, examples of which include preferably Asn, Ser, Cys, and Lys, more preferably Asn.

When the sugar chain and the amino acid is bound via a linker, the type of the linker is not particularly limited, examples of which can include —NH—(CO)—(CH$_2$)$_a$—CH$_2$— (wherein a indicates an integer which is not limited as long as it does not hinder the target linker function, preferably an integer from 0 to 4.), $C_{1-10}$ polymethylene, and —CH$_2$—R— (wherein R is a group produced by one hydrogen detached from a group selected from the group consisting of alkyl, substituted alkyl, alkenyl, substituted alkenyl, alkynyl, substituted alkynyl, aryl, substituted aryl, carbocyclic group, substituted carbocyclic group, heterocyclic group, and substituted heterocyclic group).

A "sialyl sugar chain" herein refers to a sugar chain having sialic acid at least one of the non-reducing terminals of the above sugar chain. Accordingly, for example, in the case of a tetraantennary asparagine-linked sugar chain, it comprises tetrasialo, trisialo, disialo, or monosialo form having one or more sialic acids at the non-reducing terminal, in the case of a triantennary asparagine-linked sugar chain, it comprises trisialo, disialo, or monosialo form having one or more sialic acids at the non-reducing terminal, and in the case of a biantennary asparagine-linked sugar chain, it comprises disialo or monosialo form having one or more sialic acids at the non-reducing terminal. Moreover, the position of the non-reducing terminal where the sialic acid is present is not limited.

A "sialic acid" herein is a name of a family that generically refers to a substance where the amino or hydroxy group of a neuraminic acid is substituted. Further, a "neuraminic acid" is a special nonose having an amino group and a carboxyl group within a molecule, and is represented by the following Formula.

[Chemical Formula 7]

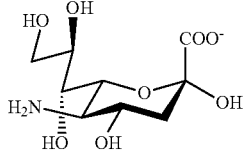

As for the sialic acid structure, known amino group substitutions for the above neuraminic acid are e.g. acetylation or glycolylation of the amino group as well as e.g. deamination where the amino group is detached, and known hydroxy group substitutions are e.g. acetylation, methylation, phosphorylation, and lactylation, but are not limited thereto.

With respect to addition of a sugar chain that occurs in nature herein, N-acetylneuraminic acid (Neu5Ac) which is the most commonly occurring in nature and N-glycolylneuraminic acid (Neu5Gc) which is the next most commonly occurring are preferred as the sialic acid that is present at the sugar chain non-reducing terminal. In particular, with respect to addition of a sugar chain that occurs in nature as a human glycoprotein, N-acetylneuraminic acid is more preferred.

A "sialylglycosylated amino acid" herein refers to the above glycosylated amino acid having a sialyl sugar chain having a sialic acid bound to at least one sugar chain non-reducing terminal.

The sialylglycosylated amino acid used in the present invention that can be used are e.g. those purified and processed from a natural product, glycoproteins synthesized in an expression system and then purified, or those chemically or enzymatically synthesized, as well as e.g. those subjected to a further sugar chain elongation reaction thereto. The sugar chain elongation reaction can be performed by selecting an enzyme that catalyzes the formation of said glycoside bond according to the glycoside binding mode of the desired sugar chain structure, and sequentially performing the above according to the binding order of sugars that constitute the sugar chain.

An example of a method for isolating a sialylglycosylated amino acid from a natural product can include a method disclosed in Japanese Patent Publication No. 2003-128703, the disclosure of which is incorporated herein in its entirety. According to this method developed by the present inventors, various isolated glycoasparagine derivatives can be obtained very easily and in large amounts compared to conventional methods.

This method is for example a method for manufacturing a glycoasparagine derivative derived from a glycoasparagine comprising the steps of:

(a) introducing a lipophilic protecting group into a glycoasparagine contained in a mixture comprising one or two or more types of glycoasparagines to obtain a glycoasparagine derivative mixture, and (b) subjecting the mixture obtained by hydrolyzing said glycoasparagine derivative mixture or the glycoasparagine derivative contained in said glycoasparagine derivative mixture to chromatography to separate each glycoasparagine derivative.

One major characteristic of this method for manufacturing a glycoasparagine derivative is, for example, introducing (binding) a lipophilic protecting group into a glycoasparagine derived from a naturally occurring glycoprotein, preferably into said glycoasparagine contained in a mixture of glycoasparagines obtained from asparagine-linked sugar chains to obtain a mixture of glycoasparagine derivatives, and then separating said mixture into each glycoasparagine derivative.

Moreover, in order to acquire the sialylglycosylated amino acid used in the present invention, it is also possible to add a sialic acid at the sugar chain non-reducing terminal of a glycosylated amino acid isolated from a natural product or a chemically/enzymatically synthesized glycosylated amino acid, by a method well-known to those skilled in the art. For example, by employing a CMP-sialic acid and sialyltransferase, sialic acid can be transferred to the sugar chain non-reducing terminal to produce a sialylglycosylated amino acid.

A "sialyltransferase" herein refers to an enzyme which is a type of glycosyltransferase, which catalyzes the reaction (hereinafter referred to as "sialic acid transfer reaction") of transferring a sialic acid residue from CMP-sialic acid that is the glycosyl donor (also referred to as a donor substrate) to the sugar chain structure that is the glycosyl acceptor (also referred to as a receptor substrate). Sialyltransferase is known to transfer sialic acid to the sugar chain non-reducing terminal. The sialic acid transfer reaction can be shown by the following reaction formula. When a sugar chain derivative is employed instead of a sugar chain, the sugar chain in the formula can be replaced with a sugar chain derivative:

[Equation 1]

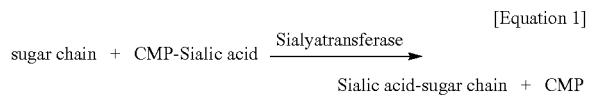

sugar chain + CMP-Sialic acid $\xrightarrow{\text{Sialyatransferase}}$ Sialic acid-sugar chain + CMP

[wherein sialic acid-sugar chain indicates a compound having a sialic acid on the sugar chain non-reducing terminal bound by a glycoside bond.]

Sialyltransferase is known to transfer to e.g. position 3 or 6 of galactose, position 6 of N-acetylgalactosamine, or position 8 of sialic acid that is present at the sugar chain non-reducing terminal. For example, the enzyme that transfers sialic acid to position 3 of galactose is called α-2,3 sialyltransferase, the enzyme that transfers sialic acid to position 6 of galactose or N-acetylgalactosamine is called α-2,6 sialyltransferase, and the enzyme that further transfers sialic acid to position 8 of sialic acid is called α-2,8 polysialyltransferase.

Known sialyltransferases are e.g. those derived from bacteria as well as rainbow trout and mammals, and proteins having sialyltransferase-like activity have also been found from plants. In particular, with respect to addition of a sugar chain that occurs in nature, those derived from mammals are preferred, and with respect to manufacture of a glycoprotein that occurs in nature as a human glycoprotein or a sugar chain thereof, those derived from human are more preferred.

Known α-2,6 sialyltransferases which are derived from human are e.g. ST6Gal-I (sometimes shown as ST6Gal1, similar applies for below) and ST6Gal-II as enzymes that transfer to position 6 of galactose, as well as ST6GalNAc-I, ST6GalNAc-11, ST6GalNAc-III, and ST6GalNAc-IV as enzymes that transfer to position 6 of N-acetylgalactosamine.

Known α-2,3 sialyltransferases which are derived from human are e.g. ST3Gal-I to ST3Gal-VI as enzymes that transfer to position 3 of galactose.

"CMP-sialic acid" herein means cytidine 5'-monophosphosialic acid, and refers to those having a structure of dehydration condensation of the hydroxy group at position 2 of sialic acid with the phosphate group of Cytidine Monophosphate (CMP). Examples of a CMP-sialic acid with the sialic acid more specifically specified include CMP-N-acetylneuraminic acid (CMP-Neu5Ac) and CMP-N-glycolylneuraminic acid (CMP-Neu5Gc). In the present specification, the CMP-sialic acid used in the present invention with respect to manufacture of a glycoprotein that occurs in nature or a sugar chain thereof is preferably CMP-N-acetylneuraminic acid (CMP-Neu5Ac) and CMP-N-glycolylneuraminic acid (CMP-Neu5Gc), and in particular, with respect to manufacture of a glycoprotein that occurs in nature as a human glycoprotein or a sugar chain thereof, CMP-N-acetylneuraminic acid (CMP-Neu5Ac) is more preferred.

Moreover, a sialic acid herein includes a sialic acid derivative, and those having the sialic acid derivative bound to the sugar chain non-reducing terminal can also be used. Sialic acid derivatives can include those having the hydroxyl group bound to the carbon at positions 7, 8, or 9 of sialic acid substituted with a hydrogen or halogen atom. Examples of a halogen atom can include fluorine, chlorine, and bromine, and may preferably be fluorine.

The sialic acid derivative can also be transferred to the sugar chain non-reducing terminal with the above transferase by producing a "CMP-sialic acid derivative." The transfer of sialic acid derivative to the sugar chain non-reducing terminal is described e.g. in International Publication No. 2004/058984, the disclosure of which is incorporated herein in its entirety.

In one aspect of the present invention, when the glycosylated amino acid having a sialic acid is an asparagine-linked sugar chain, it may or may not have a branched structure as long as it has a sialic acid at at least one of the non-reducing terminals. In addition, the branched structure is not particularly limited and selected from biantennary, triantennary, or tetraantennary. In addition, when the asparagine-linked sugar chain has a branched structure, it may only need to have a sialic acid at at least one non-reducing terminal, and depending on the number of non-reducing terminals, may have a sialic acid at one, two, three, or all terminals.

In one aspect of the present invention, when the glycosylated amino acid having a sialic acid is an asparagine-linked sugar chain, it is preferably a sugar chain having 4 or more, for example 5 or more, 7 or more, and in particular 9 or more sugars in one sugar chain.

In one preferred aspect of the present invention, when the glycosylated amino acid having a sialic acid is an asparagine-linked sugar chain, it is a sugar chain having 5-11, 9-11, or 9 sugars in one sugar chain.

In one preferred aspect of the present invention, when the glycosylated amino acid having a sialic acid is an asparagine-linked sugar chain, is a sugar chain represented by the following Formula (7):

[Chemical Formula 8]

(7)

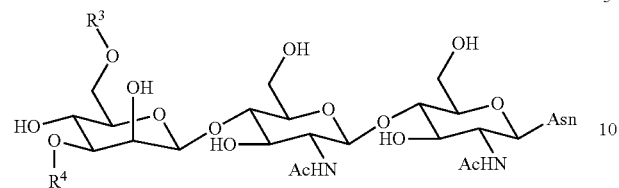

[wherein one of $R^3$ and $R^4$ is Formula (3), and the other is a hydrogen atom or a group shown in Formulae (3) to (6).]

[Chemical Formula 9]

(3)

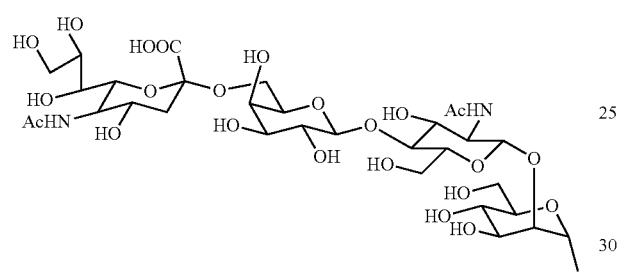

[Chemical Formula 10]

(4)

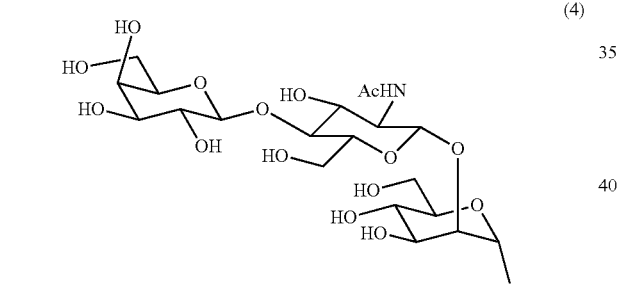

[Chemical Formula 11]

(5)

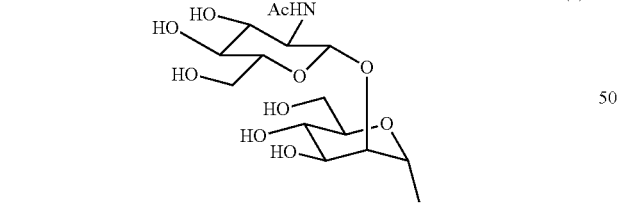

[Chemical Formula 12]

(6)

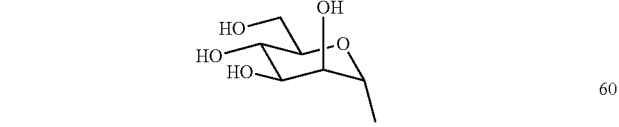

The sialylglycosylated amino acid obtained with the method above is prepared so that the amino group of an amino acid is protected with a Boc group and the carboxyl group of the sialic acid located at the non-reducing terminal on the sugar chain is protected with a phenacyl group, before employing for the solid phase synthesis method of the present invention.

"Phenacyl" herein is represented by the following Formula (provided that X is a hydrogen atom.)

[Chemical Formula 13]

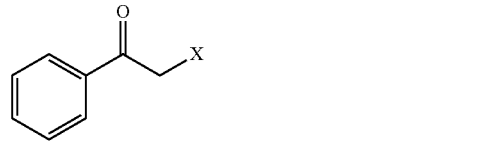

Further, examples of a phenacyl derivative suitable for the present invention include those having the above Formula wherein X=Cl or Br.

"Phenacyl group" herein is represented by the following Formula.

[Chemical Formula 14]

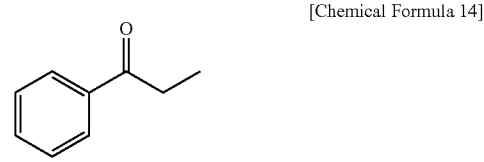

The introduction of a Boc group into the amino group of a sialylglycosylated amino acid can be performed by a conventional known method. For example, it can be introduced by adding N-(tert-butoxycarbonyloxy) succinimide (Boc-OSu) or di-tert-butyl dicarbonate [$(Boc)_2O$] in DMSO in the presence of a base (such as triethylamine and diisopropylethylamine). The reaction condition is not particularly limited, and e.g. it can be introduced at room temperature in about a few hours (1-5 hours).

Further, when a Boc-sialylglycosylated amino acid derivative is isolated by introducing Boc into a natural product, this can be used for the solid phase synthesis method of the present invention by introducing a phenacyl group directly into the Boc-sialylglycosylated amino acid derivative.

The introduction of a phenacyl group into a sialylglycosylated amino acid derivative can be carried out by e.g. dissolving the glycosylated amino acid derivative in 5 mM cesium carbonate in advance, subjecting this to lyophilization, adding DMF then phenacyl bromide to the lyophilized powder obtained, and stirring at room temperature for 6 hours or more. The pH upon dissolving in cesium carbonate is preferably within the range of 3-8, more preferably in the range of 3-4.5, most preferably 3.6.

Moreover, for example, when Fmoc is introduced into a naturally occurring sugar chain mixture comprising a sugar chain, and the isolated Fmoc-sialylglycosylated amino acid derivative is used as the raw material, a sialylglycosylated amino acid derivative having the amino group of an amino acid protected by a Hoc group and the carboxyl group of the sialic acid protected by a phenacyl group can be manufactured by a method comprising the steps of:

(a) protecting the carboxyl group of the sialic acid of a Fmoc-sialylglycosylated amino acid derivative with a phenacyl group, (b) detaching the Fmoc of said Fmoc-sialylglycosylated amino acid derivative, and (c) introducing a Boc group into the sialylglycosylated amino acid obtained in the above step.

The above steps (a) to (c) can be carried out by a method described herein or conventionally known.

By employing the Boc-sialylglycosylated amino acid derivative having the sialic acid protected with a phenacyl group obtained as above for Boc solid phase synthesis, a glycopeptide having a sialic acid at the sugar chain non-reducing terminal can be directly provided.

(Solid Phase Synthesis Method)

The solid phase synthesis of the present invention can be carried out according to a well-known method or a method similar thereto.

For example, an unglycosylated fragment can be synthesized as any amino acid sequence by the following steps (1) to (4).

(1) The hydroxyl group of a resin having a hydroxyl group and the carboxyl group of an amino acid having the amino group nitrogen protected with a Boc group are subjected to an esterification reaction. In this instance, since the amino group nitrogen of the amino acid is protected with a Boc group, self-condensation between amino acids is prevented, and the hydroxyl group of the resin and the carboxyl group of the amino acid react and esterification occur.

(2) The Boc group of the ester obtained above is detached to form a free amino group.

(3) The following steps (i) and (ii) are carried out at least once. This allows any number of arbitrary amino acids to be linked, and a peptide having the resin bound to the C-terminal and having a free amino group at the N-terminal is obtained.

(i) This free amino group and the carboxyl group of the arbitrary amino acid having the amino group nitrogen protected with a lipophilic protecting group are subjected to amidation reaction.
  (ii) The above Boc group is detached to form a free amino group.

(4) The resin is cleaved with an acid.

In addition, in case of a glycosylated fragment, the method described in e.g. International Publication No. 2004/005330 (US2005222382 (A1)) can be employed, the disclosure of which is incorporated herein by reference in its entirety.

Specifically, after synthesizing from the C-terminal to (an amino acid residue) adjacent to the amino acid to be glycosylated by the above steps (1) to (3), the carboxyl group of the sialylglycosylated amino acid derivative having the amino group nitrogen protected with a Boc group and the carboxyl group of the sialic acid protected with a phenacyl group is subjected to an amidation reaction with the free amino group of (3), and then the Boc group of the sialylglycosylated amino acid derivative is detached to form a free amino group.

Subsequently, a sialylglycosylated peptide having any amino acid sequence with a sugar chain added to any position can be obtained by repeating the above (3) for a necessary number of times, and finally cleaving the resin with an acid.

Further, a sialylglycosylated peptide having a sugar chain added at the C-terminal amino acid can be obtained if the hydroxyl group of a resin having a hydroxyl group is subjected to an esterification reaction with the carboxyl group of the sialylglycosylated amino acid derivative having the amino group nitrogen protected with a Boc group and the carboxyl group of the sialic acid protected with a phenacyl group in the above (1).

Further, a sialylglycosylated peptide having a sugar chain added at the N-terminal amino acid can be obtained if the synthesis is terminated immediately after binding the sialylglycosylated amino acid derivative having the amino group nitrogen protected with a Boc group, and then cleaving the resin with an acid.

The step of linking the sialylglycosylated amino acid can be included any number of times that is at least once or more. When included multiple times, the step of linking the sialylglycosylated amino acid may or may not be continuous, and can be appropriately set so that the addition can be at any position in the amino acid sequence of the target glycopeptide.

In one aspect of the present invention, the target glycoprotein can be produced by dividing it into several fragments, synthesizing each fragment, and then linking them by a ligation method.

In one preferred aspect of the present invention, the structure of the sialyl sugar chain manufactured can be substantially uniform. Substantially uniform sugar chain structure herein means that the glycosylation site, the types of each sugar constituting the sugar chain, the binding order, and the binding mode between sugars are identical when compared between glycopeptides having a sialyl sugar chain, and at least 90% or more, preferably 95% or more, more preferably 99% or more of the sugar chain structure is uniform. A glycopeptide having uniform sugar chains is constant in quality, and is particularly preferred in fields such as manufacturing of pharmaceutical agents or assays. The proportion of uniform sugar chains can be measured by methods employing e.g. HPLC, capillary electrophoresis, NMR, and mass spectrometry. The manufacture of sugar chain having uniform sugar chain structure is described in International Publication No. 03/008431 (US2004181054 (A1)), International Publication No. 2004/058984 (US2006228784 (A1)), International Publication No. 2004/058824 (US2006009421 (A1)), International Publication No. 2004/070046 (US2006205039 (A1)), and International Publication No. 2007/011055, the disclosures of which are incorporated herein by reference in their entirety.

The resin having a hydroxyl group may be any resin having a hydroxyl group ordinarily used in a solid phase synthesis, and e.g. Amino-PEGA resin (from Merck), Wang resin (from Merck), HMPA-PEGA resin (from Merck), and HMPB-PEGA resin (from Merck) can be employed. HMPB-PEGA resin is preferred with respect to subjecting to thioesterification after solid phase synthesis.

Any amino acid can be employed as the amino acid, examples of which can include the naturally occurring amino acids serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenyl alanine (Phe), tryptophan (Trp), and proline (Pro). Moreover, examples of a non-naturally occurring amino acid include D-amino acids; chemically modified amino acids such as amino acid variants and derivatives; norleucine, β-alanine, and ornithine.

Because the solid phase synthesis method of the present invention uses protection with a Boc group as the protecting group for the amino group of an amino acid, and detaches the BoC group under acidic condition after solid phase synthesis, it is possible to synthesize a glycopeptide using a base-labile non-naturally occurring amino acid. A "base-labile non-naturally occurring amino acid" herein refers to a non-naturally occurring amino acid of which the chemical structure collapses by e.g. breaks in chemical bond under basic condition, in particular under the detachment condition of Fmoc in the Fmoc solid phase synthesis method. Further, since the Boc solid phase synthesis method does not utilize a base as shown above, a base-labile peptide thioester can be produced directly in the solid phase synthesis.

Boc group can be introduced by a condition similar to the condition for introduction into the above sialylglycosylated amino acid.

Meanwhile, a solid phase synthesis method employing a Boc group as the lipophilic protecting group is referred to as the Boc solid phase synthesis method.

For amino acids protected with a Boc group, the above amino acid can be manufactured with the above method. Those commercially available can also be used. Examples can include Boc-Ser, Boc-Asn, Boc-Val, Boc-Leu, Boc-Ile, Boc-Ala, Boc-Tyr, Boc-Gly, Boc-Lys, Boc-Arg, Boc-His, Boc-Asp, Boc-Glu, Boc-Gln, Boc-Thr, Boc-Cys, Boc-Met, Boc-Phe, Boc-Trp, and Boc-Pro. Moreover, a non-naturally occurring amino acid protected with a Boc group can be manufactured in a method similar to the protection of amino acids. Those commercially available can also be used.

In addition, examples of an amino acid protected with a lipophilic protecting group having a protecting group introduced into the side chain can include Boc-Arg(di-Z), Boc-Asn(Xan), Boc-Asp(Bn), Boc-Cys(Acm), Boc-Glu(Bn), Boc-His(DNP), Boc-Lys(Cl—Z), Boc-Ser(Bn), Boc-Thr(Bn), Boc-Trp(CHO), and Boc-Tyr(Br-Z).

In addition, Thz herein indicates the thiazolidine-type of Cys (Thiazolidine-4-carboxylic acid). Moreover, (di-Z) indicates a dicarbobenzoxy group (N,N-Bis-(benzyloxycarbonyl)-), (Xan) indicates a xanthyl group, (Bn) indicates a benzyl group, (Acm) indicates an acetamidomethyl group, (tBu) indicates a tert-butyl group, (Trt) indicates a trityl group, (DNP) indicates a 2,4-dinitrophenyl group, (Cl—Z) indicates a [(2 chlorophenyl)methoxy]carbonyl group, and (CHO) indicates a formyl group.

Well-known dehydration condensation agents such as 1-mesitylenesulfonyl-3-nitro-1,2,4-triazole (MSNT), dicyclohexylcarbodiimide (DCC), and diisopropylcarbodiimide (DIPCDI) can be employed as an esterification catalyst. The proportion of use between the amino acid and the dehydration condensation agent is 1 part by weight of the former to ordinarily 1-10 parts by weight, preferably 2-5 parts by weight of the latter.

The esterification reaction is preferably carried out for example by placing the resin in a solid phase column, washing this resin with a solvent, and then adding the amino acid solution. Examples for a washing solvent can include dimethylformamide (DMF) and methylene chloride. Examples of a solvent for dissolving the amino acid can include dimethyl sulfoxide (DMSO), DMF, and methylene chloride. The esterification reaction may be carried out at 0-50° C., preferably at room temperature for about 10 minutes to about 2 hours, preferably about 5-15 minutes.

It is also preferred to acetylate the unreacted hydroxyl group on the solid phase at this time with e.g. acetic anhydride for capping.

The detachment of the Boc group can be carried out for example by treating with an acid. Examples of an acid can include 10% sulfuric acid/dioxane solution, 50% trifluoroacetic acid/methylene chloride, and p-toluenesulfonic acid/tetrahydrofuran-methylene chloride.

The amidation reaction of free amino group with the carboxyl group of an arbitrary amino acid having the amino group nitrogen protected with a Boc group is preferably carried out in the presence of an activator and a solvent.

Examples of an activator can include dicyclohexylcarbodiimide (DCC), 1-ethyl-3-(3-dimethylaminopropyl)carbodiimide hydrochloride (WSC/HCl), diphenyl phosphorylazide (DPPA), carbonyldiimidazole (CDI), diethyl cyanophosphonate (DEPC), diisopropylcarbodiimide (DIPCI), benzotriazol-1-yloxy-tris-pyrrolidinophosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazol-1-yl)-1,1,3,3-tetramethyluronium hexafluorophosphate (HBTU), O-(7-azabenzotriazol-1-yl)-1,1,3,3-tetramethyluronium hexafluorophosphonate (HATU), O-benzotriazol-1-yl-1,1,3,3-tetramethyluronium tetrafluoroborate (TBTU), and 3,4-dihydro-3-hydrodi-4-oxa-1,2,3-benzotriazine (Dhbt).

The amount of the activator to be used is preferably 0.8-10 equivalents, preferably 0.8-2 equivalents, further preferably, 0.95 equivalents relative to the arbitrary amino acid having the amino group nitrogen protected with a Boc group.

Examples of a solvent can include DMSO, DMF, and methylene chloride. The reaction may be carried out at 0-50° C., preferably at room temperature for about 10 minutes to about 2 hours, preferably about 5-15 minutes.

It is preferred that the peptide chain is cleaved from the resin by treating with an acid. Examples of an acid can include super strong acids such as trifluoroacetic acid/trifluoromethanesulfonic acid (TfOH), hydrogen fluoride (HF), methanesulfonic acid, and a mixed acid of trifluoroacetic acid/trifluoromethanesulfonic acid/dimethyl sulfide/m-cresol.

The sugar chain employed in the present invention may have the hydroxyl group on the sugar chain thereof protected. Examples of a protecting group can include an acetyl group and a triethylsilyl group. It is preferably a protecting group that can be treated with an acid simultaneously with the cleaving from the synthesized glycopeptide, and an example thereof can include a triethylsilyl group.

It may also be preferred to employ a microwave method for the solid phase synthesis method in the present invention. An example of a microwave method is described in Bacsa B. et al., J. Org. Chem. (2008) 73:7532-7542, the disclosure of which is incorporated herein by reference in its entirety.

The microwave method is a method of irradiating microwave in the amino acid condensation step or the deprotection step to solve problems based on e.g. intramolecular aggregation or formation of secondary structure and steric hindrance due to the protecting group, and is useful for synthesizing a peptide that is difficult to synthesize in an ordinary method, in particular a long-chain peptide. The condition of microwave irradiation can be appropriately determined by those skilled in the art according to the amino acid sequence so that side reactions occurring due to application of heat or energy during reaction can be prevented.

(C-Terminal Thioesterification)

In addition, one aspect of the present invention can produce glycopeptide fragments for linking by ligation to manufacture the glycoprotein of interest. In other words, the C-terminal of the glycopeptide fragment having a sialyl sugar chain manufactured can be thioesterified, i.e. an α-carboxythioester moiety can be formed at the C-terminal, for ligation. A well-known method or a method similar thereto can be employed for the method for manufacturing peptide fragments (or glycopeptide fragments) having an α-carboxythioester moiety represented by —C(=O)—SR at the C-terminal. Such a method is described e.g. in International Publication No. 96/34878 (U.S. Pat. No. 6,184,344), the disclosure of which is incorporated herein by reference in its entirety.

R herein is not particularly limited provided that it is a group that does not inhibit thiol exchange reaction and becomes a leaving group in the nucleophilic substitution reaction to the carbonyl carbon, but can be preferably selected from e.g. a benzyl-type such as benzyl mercaptan, an aryl-type such as thiophenol and 4-(carboxymethyl)-thiophenol, and an alkyl type such as 2-mercaptoethanesulfonate salt and 3-mercaptopropionic amide.

Examples of a method for manufacturing a peptide fragment having an α-carboxythioester moiety at the C-terminal include, specifically, a method of performing thioesterification when cleaving out the peptide from the solid phase, or a method of thioesterifying the C-terminal carboxyl group of the peptide after cleaving out the peptide from the solid phase. As a method of performing thioesterification when cleaving out the peptide from the solid phase, for example a method of employing a Safety Catch Linker (sulfamide linker) on the solid phase resin to manufacture the peptide and allowing a thiol compound to act therewith is known (J. Am. Chem. Soc., (1999) 121:11369-11374, Angew. Chem. Int. Ed., (2005) 44:1650-1654).

However, it is required to alkylate the sulfamide linker in the above method, and there are restrictions that its alkylation efficiency is poor and the resin to be used is expensive.

Another method of manufacturing a peptide fragment having an α-carboxythioester moiety at the C-terminal is a method of obtaining the thioester form when cleaving out the peptide from the resin by binding the thioester form to the resin at the start of solid phase synthesis. This method cannot be applied to Fmoc solid phase synthesis method which requires a base for the detachment reaction of the lipophilic protecting group, but can be applied to the Boc solid phase synthesis method of the present invention. For example, a peptide thioester can be produced when the peptide produced from the resin is cleaved off, by linking amino acids after subjecting the mercaptopropionic acid to thioester binding with the resin.

In one aspect of the present invention, the step of preparing the glycopeptide fragment and the step of thioesterifying the C-terminal of the glycopeptide fragment may be carried out simultaneously.

As a method of simultaneously carrying out the step of preparing the glycopeptide fragment and the step of thioesterifying the C-terminal of the glycopeptide fragment, for example, a fusion protein having the amino acid sequence of intein added at the C-terminal side of each glycopeptide fragment can be prepared, and the intein can be cleaved by intein reaction while at the same time thioesterifying the C-terminal of the fragment. Such a method is described e.g. in Muralidharan V, et al. (Nature Methods (2006) Vol. 3 No. 6 429-438), the disclosure of which is incorporated herein by reference in its entirety.

The glycopeptide fragment can also be linked with the KCL method. When the KCL method is employed, the thioester at the C-terminal of the first glycopeptide fragment must be provided as a thioester having higher detachment ability than the thioester at the C-terminal of the second glycopeptide fragment. By doing so, the second glycopeptide fragment can be bound to the C-terminal of the first glycopeptide fragment side by the difference in reaction rate, and the production of incorrectly linked byproduct etc. can be suppressed.

In general, since the reactivity of thiol groups is in the order of aryl thiol group>benzyl-type thiol group>alkyl-type thiol group, according to this order, a thiol group having higher reactivity than the C-terminal of one peptide fragment is provided on the C-terminal of the other peptide fragment.

For example, the combination of the C-terminal of the first glycopeptide fragment being a thiophenyl ester and the C-terminal of the second glycopeptide fragment being an ethyl thioester; the combination of the C-terminal of the first glycopeptide fragment being 4-mercaptophenyl thioester (MPAA) and the C-terminal of the second glycopeptide fragment being a benzyl thioester; and the combination of the C-terminal of the first glycopeptide fragment being a thiophenyl ester and the C-terminal of the second glycopeptide fragment being a mercaptoethanesulfonyl ester are preferred.

The —SH group of the N-terminal Cys of the glycopeptide fragment may also be protected by a protecting group as desired. For example, the —SH group may be protected as thiazolidine. This protecting group is deprotected at a desired time before the ligation reaction. For example, a protecting group that is naturally deprotected under the condition ligation occurs such as a disulfide group can be directly employed in the following ligation reaction without deprotection. The disulfide group is easily deprotected under the reaction condition of the subsequent ligation method.

(Linking Step by Ligation Method)

In one aspect of the present invention, the glycopeptide fragment manufactured by the manufacturing method of the present invention can be linked with another peptide fragment or another glycopeptide fragment by a method well-known to those skilled in the art. Another peptide fragment and another glycopeptide fragment to be employed can be a fragment obtained by a method not limited to the Boc solid phase synthesis method but also a method well-known to those skilled in the art such as Fmoc solid phase synthesis method as well as other chemical synthesis and biosynthesis.

For example, two glycopeptide fragments are mixed in a solution such as 100 mM phosphate buffer, in the presence of a catalytic thiol such as 4-mercaptophenyl acetic acid, benzyl mercaptan, and thiophenol as necessary. Preferably, the reaction is carried out at a proportion of 0.5-2 equivalents of the second glycopeptide fragment and about 5 equivalents of the catalytic thiol to 1 equivalent of the first glycopeptide fragment. The reaction is desirably carried out under a condition of at about pH 6.5-7.5 and about 20-40° C. for about 1-30 hours. The progress of the reaction can be confirmed with a well-known method combining HPLC and MS etc.

To this was added a reductant such as tris-2-carboxyethyl phosphine hydrochloride (TCEP) to suppress side reactions, and purified as desired to allow linking of the first and second peptide fragments.

Moreover, the KCL method is an NCL method reported by Kent with reaction kinetic control (Kent et al., Angew. Chem. Int. Ed., 2006, 45, 3985-3988). The NCL method is a method where the C-terminal of one of the two fragments to be linked is a carboxyl group and the C-terminal of the other is thioesterified, and the other fragment is bound to the C-terminal side of the thioesterified fragment. On the other hand, the KCL method can be employed when both of the fragments to be linked are thioesterified, and the thioester with a higher detachment ability will be subjected to the linking reaction.

As described above, the reactivity of thiol groups is generally in the order of aryl thiol group>benzyl-type thiol group>alkyl-type thiol group. Accordingly, the C-terminal thioester —C(=O)—SR has the highest detachment ability when R is an aryl group, followed by when R is a benzyl group and when R is an alkyl group. By determining the thioester of each fragment based on this, each fragment can be linked in the desired order. For example, when one is a thiophenyl ester and the other is an ethyl thioester, the thiophenyl ester is subjected first to the linking reaction and a peptide having an ethyl thioester at the C-terminal is obtained. When one is 4-mercaptophenyl thioester (MPAA) and the other is a benzyl thioester, MPAA is reacted first to afford a peptide having a benzyl thioester at the C-terminal, and when one is a thiophenyl ester and the other is a mercaptoethanesulfonyl ester, the thiophenyl ester is reacted first to afford a peptide having a mercaptoethanesulfonyl ester at the C-terminal.

As such, since a peptide chain obtained by the KCL method has a thioester at the C-terminal, the peptide chain can be directly employed for ligation with another fragment.

(Folding Step)

Further, in another aspect of the present invention, after manufacturing the glycopeptide having a sialyl sugar chain, the fragments can treated so that they are linked and subjected to a folding step to assume appropriate conformation.

Various well-known methods can be employed for the folding step; it can for example be carried out by dialysis in a folding buffer. The folding buffer comprises e.g. a compound having a guanidino group such as guanidine or a salt thereof, and may have a pH of between 6.0 and 9.0. Dialysis may be performed multiple times, in which case the composition or the pH of the buffer for each dialysis treatment may be the same or different.

The folding of the polypeptide can be confirmed by any method of analyzing the conformation of a polypeptide, examples of which include, but are not limited to, disulfide mapping method, evaluation of binding to antibody specific to a conformational epitope, and X-RAY analysis.

The terms used herein are to be employed to describe particular embodiments, and do not intend to limit the invention.

The term "comprising" as used herein, unless the context clearly indicates to be understood otherwise, intends the presence of the described items (such as components, steps, elements, and numbers), does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meaning.

The embodiments of the present invention may be described referring to schematic diagrams. In case of schematic diagrams, they may be exaggerated in presentation in order to allow clear description.

Terms such as first and second are employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The present invention will now be described in further detail referring to Examples. However, the present invention can be embodied by various aspects, shall not be construed as being limited to the Examples described herein.

EXAMPLES

Example 1

Synthesis of Boc-diphenacyl-disialoglycoasparagine (Boc-diphenacyl-disialooligo-asparagine)

(I) Synthesis of Fmoc-diphenacyl-disialoglycoasparagine (Fmoc-diphenacyl-disialooligo-asparagine)

Fmoc-disialoglycoasparagine (Fmoc-disialooligo-asparagine) (20 mg) was dissolved in 2 ml of ice water, the Fmoc-disialoglycoasparagine dissolved in ice water was passed through Dowex-50×8($H^+$) resin (10.5 cm×5 cm), and the eluted solution was lyophilized. The lyophilized solution was dissolved in 10 ml of water, and 5 mM aqueous cesium carbonate ($Cs_2CO_3$) solution was used to adjust the solution to pH 3.6. The solution was then lyophilized again. The Fmoc-disialoglycoasparagine after lyophilization was dissolved in dry DMF (4 ml), and phenacyl bromide (5.7 mg) was added. After 8 hours, diethyl ether (20 ml) was added to this mixed solution, and the target object was precipitated. This was filtered though a filter paper. The remaining precipitate was collected, a solution of water:acetonitrile=7:3 was added to the precipitate and allowed to dissolve, and this was purified by HPLC. The above operations enabled to afford the target Fmoc-diphenacyl-disialoglycoasparagine (16 mg, 76% yield).

Fmoc-diphenacyl-disialooligo-asparagine

ESI-MS: calcd for $C_{119}H_{166}N_8O_{68}$: 2796.6 $[M+H]^+$, 1399.3 $[M+2H]^{2+}$. found: 2798.2 $[M+H]^+$, 1399.6 $[M+2H]^{2+}$.

(II) Synthesis of Boc-diphenacyl-disialoglycoasparagine (Boc-diphenacyl-disialooligo-asparagine)

To Fmoc-diphenacyl-disialoglycoasparagine (Fmoc-diphenacyl-disialooligo-asparagine) (20 mg) was added 1-methylpyrrolidine (75 µL), hexamethyleneimine (2 µL), and HOBt (2 mg) dissolved in dry DMF (100 µL), and this was stirred at ordinary temperature and allowed to dissolve. After 30 minutes, diethyl ether was further added, and diphenacyl-disialoglycoasparagine with Fmoc detached was precipitated. The precipitate was collected, diethyl ether was evaporated, and then the precipitate was dissolved in distilled water. The precipitate dissolved in distilled water was passed through Shephadex G-15 for purification, and then the eluted solution was lyophilized. The diphenacyl-disialoglycoasparagine obtained was dissolved in DMF (1 mL), $Boc_2O$ (4.8 µL) was added and stirred at ordinary temperature to introduce a Boc group. After 4 hours, diethyl ether was added and the precipitate was collected. The precipitate was dissolved in 50 mM ammonium acetate:water=82:17 and purified by HPLC. The above operations enabled to afford the target Boc-diphenacyl-disialoglycoasparagine (13 mg, 68% yield).

Boc-diphenacyl-disialooligo-asparagine

ESI-MS: calcd for $C_{109}H_{164}N_8O_{68}$: 2674.5 $[M+H]^+$, 1338.2 $[M+2H]^{2+}$. found: 2675.8 $[M+H]^+$, 1338.4 $[M+2H]^{2+}$.

Example 2

Synthesis of Glycopeptide Thioester Form (TN(diphenacyl-disialo sugar chain)YSVTDLNY-SR) (SEQ ID NO:1)

I) Preparation of Peptide Chain

Solid phase synthesis was carried out with a Prostyrene column (Tokyo Rika, No. 183 470). Amino-PEGA resin (50 µmol, 1.67 g) was placed in a Prostyrene column, and sufficiently conditioned with DMF solvent. Subsequently, a solution of S-trityl-3-mercaptopropionic acid (200 μmol), HBTU (190 μmol), and DIPEA (800 μmol) dissolved in DMF was added to the amino-PEGA resin, and this was stirred at ordinary temperature. After 30 minutes, the resin was washed with DMF and DCM, and 95% TFA and 5% TIPS were added. After 2 minutes, the solution was filtered, TFA and TIPS were added again, and after 2 minutes, the resin was washed with DMF. To this resin, a mixed solution of Boc-Tyr(OBn)-OH (200 mM), HBTU (190 mM), and DIPEA (400 mM) dissolved in DMF was added to the resin to allow the condensation of the first amino acid residue tyrosine. After 20 minutes, the resin was successively washed with DMF and dioxane. To this resin, 10% sulfuric acid/dioxane solution was added, filtered after 5 minutes, the same solution was further added, and stirred for 30 minutes to carry out the deprotection of the Boc group. Subsequent amino acids (Boc-Asn(Xan)-OH, Boc-Leu-OH, Boc-Asp(OBn)-OH, Boc-Thr(OBn)-OH, Boc-Val-OH, Boc-Ser(OBn)-OH, and Boc-Tyr(OBn)-OH) were condensed in a similar method.

II) Condensation of Sialylglycosylated Amino Acid and Subsequent Amino Acid Condensation After deprotecting the Boc group of the resin having the peptide thioester elongated (2 μmol) with the above method, this was washed with DMF, and 5% DIPEA/DMF was added. After 1 minute, this was washed well with DMF, a solution of Boc-diphenacyl-disialoglycoasparagine (4 μmol), DEPBT (6 μmol), and DIPEA (4 μmol) dissolved in DMF was added, and stirred at ordinary temperature. After 14 hours, the resin was washed well with DMF. In subsequent peptide elongation (Boc-Tyr(OBn)-OH), condensation was carried out with a method similar to the above at an amino acid concentration of 40 mM in order to prevent side reactions of the sugar chain hydroxyl group.

III) Deprotection of Amino Acid Side Chain and Cleaving Out from Resin

After washing the resin with DCM, a cocktail cooled to 0° C. comprising TFA (350 μL), DMS (210 μL), m-cresol (70 μL), and TfOH (70 μL) was added, and stirred at 0° C. After 30 minutes, the solution was filtered, the resin was washed with TFA, diethyl ether, DMF, DCM, and TFA in this order, the same amount of the above cocktail was added again, and stirred at 0° C. After 2 hours, the solution was filtered, and the resin was washed well with TFA, diethyl ether, and DMF in this order. MESNa (5 mg) was dissolved in 200 m phosphate buffer (95 μL) containing 6 M guanidine hydrochloride, and added to this resin. After 12 hours, the compound contained in the eluted solution was analyzed and purified by HPLC. As a result, this enabled to afford a glycopeptide (1) having diphenacyl-disialoglycoasparagine and having the amino acid sequence TN(diphenacyl-disialo sugar chain)YSVT-DLNY-SR (SEQ ID NO:1). Note that in the said amino acid sequence, N(diphenacyl-disialo sugar chain) indicates a glycoasparagine and —SR indicates a sulfonic acid ethyl thioester.

Example 3

Synthesis of Glycopeptide Thioester Form Having Sialyl Sugar Chain (SLQN(diphenacyl-disialo sugar chain)ASAIES-SR) (SEQ ID NO:2)

I) Preparation of Peptide Thioester Form

Solid phase synthesis was carried out with a Prostyrene column (Tokyo Rika, No. 183 470). Amino-PEGA resin (50 μmol, 1.67 g) was placed in a Prostyrene column, and sufficiently conditioned with DMF solvent. Subsequently, a solution of S-trityl-3-mercaptopropionic acid (200 μmol), HBTU (190 μmol), and DIPEA (800 μmol) dissolved in DMF was added to the amino-PEGA resin, and this was stirred at ordinary temperature. After 30 minutes, the resin was washed well with DMF and DCM, and 95% TFA and 5% TIPS were added. After 2 minutes, the solution was filtered well, TFA and TIPS were added again, and after 2 minutes, the resin was washed well with DMF. To this resin, a mixed solution of Boc-Ser(OBn)-OH (200 mM), HBTU (190 mM), and DIPEA (400 mM) dissolved in DMF was added to the resin to allow the condensation of the first amino acid residue serine. After 20 minutes, the resin was successively washed with DMF and dioxane. To this resin, 10% sulfuric acid/dioxane solution was added, filtered after 5 minutes, the same solution was further added, and stirred for 30 minutes to carry out the deprotection of the Boc group. Subsequent amino acids (Boc-Glu(OBn)-OH, Boc-Ile-OH, Boc-Ala-OH, Boc-Ser(OBn)-OH, and Boc-Ala-OH) were condensed in a similar method.

II) Condensation of Sialylglycosylated Amino Acid and Subsequent Amino Acid Condensation After deprotecting the Boc group of the resin having the peptide thioester elongated (2 μmol) with the above method, this was washed with DMF, and 5% DIPEA/DMF was added. After 1 minute, this was washed well with DMF, a solution of Boc-diphenacyl-disialoglycoasparagine (4 μmol), DEPBT (6 μmol), and DIPEA (4 μmol) dissolved in DMF was added, and stirred at ordinary temperature. After 14 hours, the resin was washed well with DMF. Condensation of sugar chain was carried out again under the above condition. In subsequent peptide elongation (Boc-Gln-OH, Boc-Leu-OH, Boc-Ser(OBn)-OH), condensation was carried out with a method similar to the above at an amino acid concentration of 40 mM in order to prevent side reactions of the sugar chain hydroxyl group.

III) Deprotection of Amino Acid Side Chain and Cleaving Out from Resin

After washing the resin with DCM, a cocktail cooled to 0° C. comprising TFA (350 μL), DMS (210 μL), m-cresol (70 μL), and TfOH (70 μL) was added, and stirred at 0° C. After 30 minutes, the solution was filtered, the resin was washed with TFA, diethyl ether, DMF, DCM, and TFA in this order, the same amount of the above cocktail was added again, and stirred at 0° C. After 2 hours, the solution was filtered, and the resin was washed well with TFA, diethyl ether, and DMF in this order. MESNa (5 mg) was dissolved in 200 m phosphate buffer (95 μL) containing 6 M guanidine hydrochloride, and added to this resin. After 12 hours, the compound contained in the eluted solution was analyzed and purified by HPLC. As a result, this enabled to afford a glycopeptide (2) having diphenacyl-disialoglycoasparagine and having the amino acid sequence SLQN(diphenacyl-disialo sugar chain)ASAIES-SR (SEQ ID NO:2). Note that in the said amino acid sequence, N(diphenacyl-disialo sugar chain) indicates a glycoasparagine and —SR indicates a sulfonic acid ethyl thioester.

Glycopeptide-thioester

ESI-MS: calcd for $C_{143}H_{222}N_{18}O_{83}S_2$: 3585.5, $[M+H]^+$, 1793.8 $[M+2H]^{2+}$, 1196.2 $[M+3H]^{3+}$;

found: 3586.9, $[M+H]^+$, 1794.0 $[M+2H]^{2+}$, 1196.3 $[M+3H]^{3+}$.

Abbreviation of Reagents:

DMF: N,N-dimethylformamide, DCM: dichloromethane, HOBt: 1-hydroxybenzotriazole, TFA: trifluoroacetic acid, DEPBT: 3-(Diethoxy-phosphoryloxy)-3H-benzo[d][1,2,3]triazin-4-one, HBTU: 2-(1H-Benzotriazole-1-yl)-1,1,3,3-tetramethyluronium hexafluorophosphate, DIPEA: N,N-diisopropylethylamine

Example 4

Synthesis of Erythropoietin (I) Synthetic Scheme of Erythropoietin

Native erythropoietin has a sequence of 166 amino acids, and has asparagine (N)-linked sugar chains at positions 24, 38, and 83 and an O-linked sugar chain that binds to serine at position 126. In the following Examples, a glycopeptide was synthesized where the amino acid sequence has the glycosylated asparagine at positions 24 and 38 converted to unglycosylated asparagine, the glutamic acid at position 21 converted to cysteine, the glutamine at position 78 converted to cysteine, and the glycosylated serine at position 126 converted to unglycosylated serine in the native erythropoietin amino acid sequence, as well as has sialylglycoasparagine at position 83 of the amino acid sequence. Cysteines inserted instead of glutamic acid at position 21 and glutamine at position 78 were used for linking sites of ligation. The present Examples exemplify a method of manufacturing 1 to 166 amino acids of the amino acid sequence of erythropoietin divided into 6 fragments of: peptide fragment A having amino acids from positions 1 to 21, peptide fragment B having amino acids from positions 22 to 49, peptide fragment C having amino acids from positions 50 to 78, glycosylated peptide fragment D having amino acids from positions 79 to 97, peptide fragment E having amino acids from positions 98 to 127, and peptide fragment F having amino acids from positions 128 to 166.

More specifically, a manufacturing method comprising the following steps is exemplified.

(A) Step of Producing Peptide Fragment A Represented by the Following Formula (8), Peptide Fragment B Represented by the Following Formula (9), Peptide Fragment C Represented by the Following Formula (10), glycosylated Peptide Fragment D Represented by the Following Formula (11), Peptide Fragment E Represented by the Following Formula (12), and Peptide Fragment F Represented by the Following Formula (13).

[Chemical Formula 15]

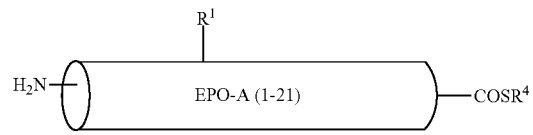

(8)

[Chemical Formula 16]

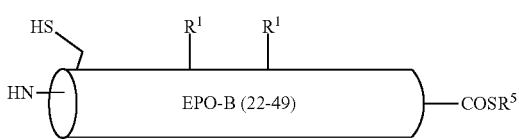

(9)

[Chemical Formula 17]

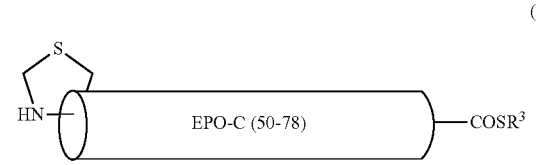

(10)

[Chemical Formula 18]

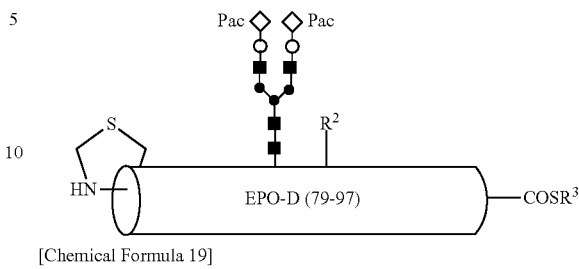

(11)

[Chemical Formula 19]

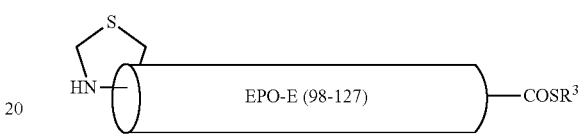

(12)

[Chemical Formula 20]

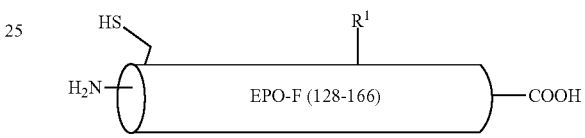

(13)

In the above formulae, $R^1$ represents an Acm group. Fragments A, B, and F each have a cysteine having an Acm group at positions corresponding to positions 7, 29, 33, and 161 in the native erythropoietin amino acid sequence. In addition, $R^2$ indicates a formyl group (CHO). Fragment D has a tryptophan protected with a formyl group at a position corresponding to position 88 in the native erythropoietin amino acid sequence. In addition, $R^3$ together with an adjacent S (sulfur) indicates a sulfonic acid ethyl thioester, $R^4$ indicate a phenyl group, and $R^5$ indicates a benzyl group.

In each fragment, the C-terminal used for linking by ligation is thioesterified. Moreover, in each fragment, the N-terminal used for linking by ligation has a cysteine. Peptide fragment C, glycosylated peptide fragment D, and peptide fragment E represented by the above Formulae also have the cysteine on the N-terminal side as a thiazolidine-type in order to avoid side reactions in the ligation step at respective C-terminal sides.

The N-terminal amino acids of the above fragment B, fragment C, glycosylated fragment D, fragment E, and fragment F are alanine at positions 22, 50, 79, 98, and 128 in the native erythropoietin amino acid sequence. However, in the present Example, cysteine is required on the N-terminal of the fragment to be linked in the ligation step. Accordingly, the N-terminal amino acids of fragment B, fragment C, glycosylated fragment D, fragment E, and fragment F are synthesized as cysteine instead of alanine in each manufacture example. The cysteine substituted instead of alanine was reduced to alanine after ligation between each fragment.

Figure 5:
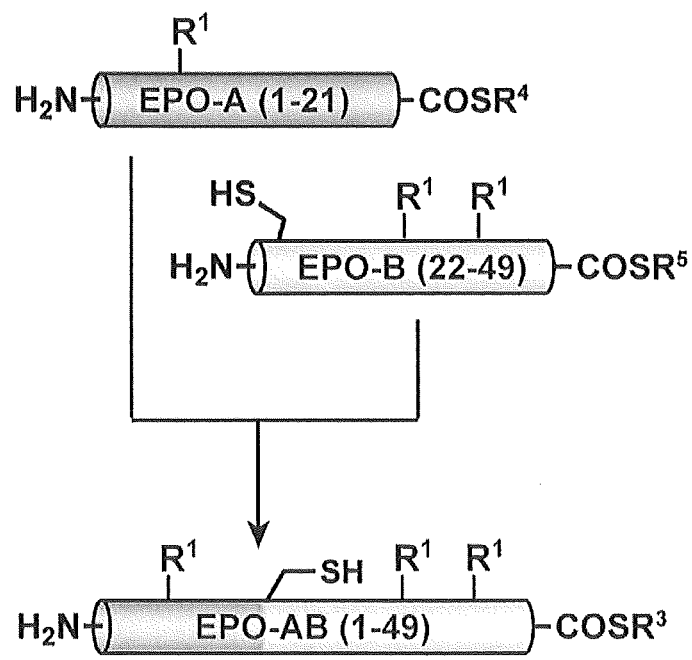
FIG. 5 is a schematic diagram showing one embodiment of the present invention, which is a part of a step of a method for manufacturing an amino acid sequence having a biantennary disialoglycoasparagine using erythropoietin as the model peptide. Specifically, it is a schematic diagram showing the step of linking fragment A having the amino acid sequence of amino acid sequences 1-21 of erythropoietin with fragment B having the amino acid sequence of amino acid sequences 22-49 of erythropoietin to produce fragment (A+B).

(B) Step of Linking Fragment A and Fragment B by Ligation to Produce Fragment (A+B) (see FIG. 5).

In the present specification, for example, fragment (A+B) indicates a fragment obtained by linking the C-terminal of fragment A and the N-terminal of fragment B.

Figure 6:
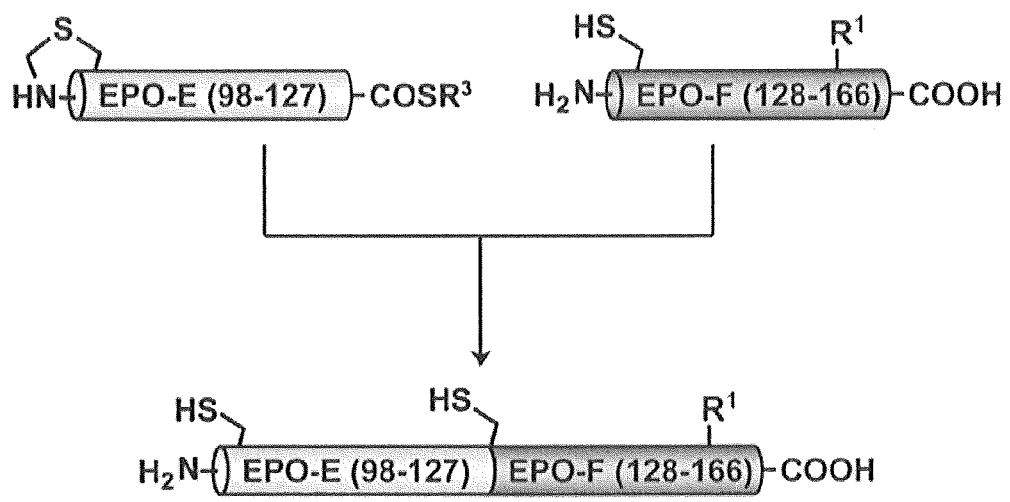
FIG. 6 is a schematic diagram showing one embodiment of the present invention, which is a part of a step of a method for manufacturing an amino acid sequence having a biantennary disialoglycoasparagine using erythropoietin as the model peptide. Specifically, it is a schematic diagram showing the step of linking fragment E having the amino acid sequence of amino acid sequences 98-127 of erythropoietin with fragment F having the amino acid sequence of amino acid sequences 128-166 of erythropoietin to produce fragment (E+F), and the step of converting the N-terminal thiazolidine-type cysteine of fragment (E+F) into cysteine.

(C) Step of Linking Fragment E and Fragment F by Ligation to Produce Fragment (E+F), and Step of Converting N-Terminal Thiazolidine-Type Cysteine of Fragment (E+F) into Cysteine (see FIG. 6).

Figure 9:
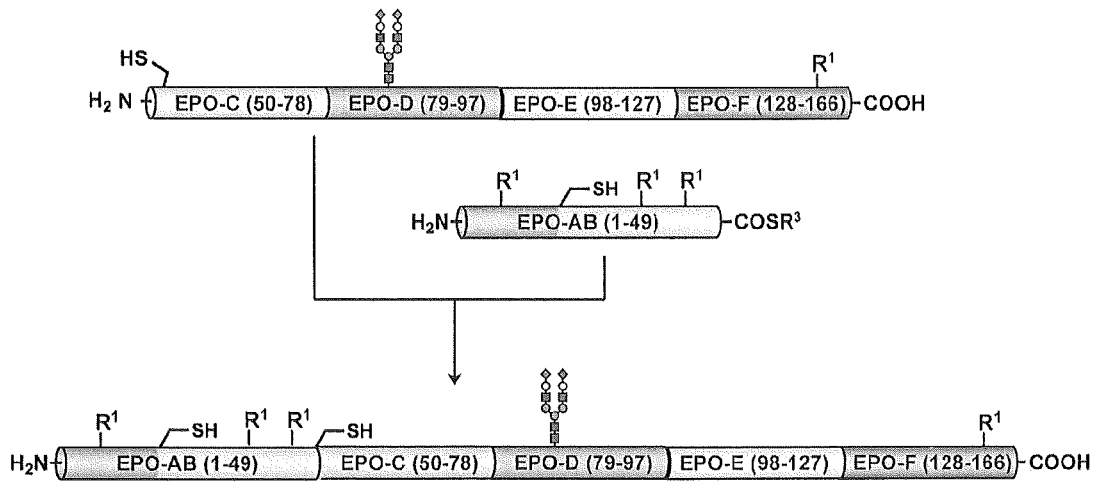
FIG. 9 is a schematic diagram showing one embodiment of the present invention, which is a part of a step of a method for manufacturing an amino acid sequence having a biantennary disialoglycoasparagine using erythropoietin as the model peptide. Specifically, it is a schematic diagram showing the step of linking fragment (C+D+E+F) having the amino acid sequence of amino acid sequences 50-166 of erythropoietin with fragment (A+B) having the amino acid sequence of amino acid sequences 1-49 of erythropoietin to produce fragment (A+B+C+D+E+F).
Figure 10:
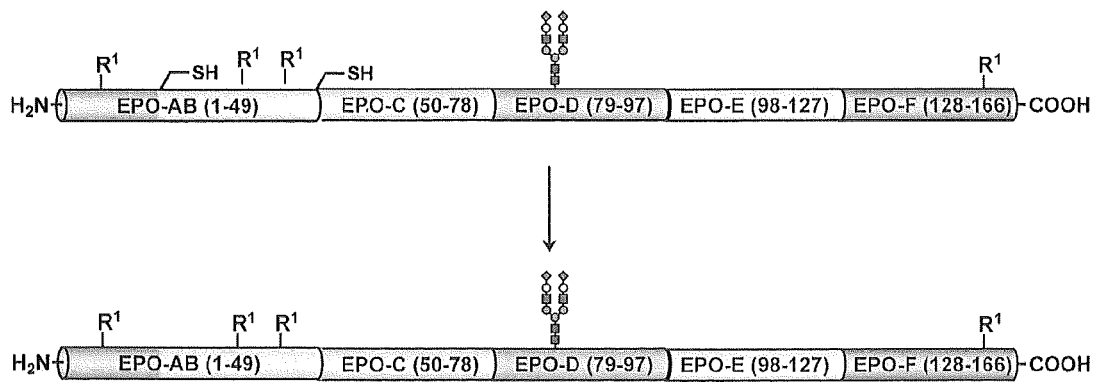
FIG. 10 is a schematic diagram showing one embodiment of the present invention, which is a part of a step of a method for manufacturing an amino acid sequence having a biantennary disialoglycoasparagine using erythropoietin as the model peptide. Specifically, it is a schematic diagram showing the step of converting the cysteine employed for ligation into alanine in fragment (A+B+C+D+E+F) having the amino acid sequence of amino acid sequences 1-166 of erythropoietin.

(D) Step of Linking Fragment D and Fragment (E+F) by Ligation to Produce Fragment (D+E+F), Step of Converting N-Terminal Thiazolidine-Type Cysteine of Fragment (D+E+F) into Cysteine, and Step of Removing Formyl (CHO) Group on Tryptophan and Phenacyl Group on Sugar Chain Sialic Acid (see FIG. 7)
(E) Step of Linking Fragment C and Fragment (D+E+F) by Ligation to Produce Fragment (C+D+E+F), Reducing Cysteine Employed for Ligation into Alanine, and Converting N-Terminal Thiazolidine-Type Cysteine of Fragment (C+D'+E+F) into Cysteine (see FIG. 8)
(F) Step of Linking Fragment (A+B) and Fragment (C+D+E+F) by Ligation to Produce Fragment (A+B+C+D+E+F) (see FIG. 9)
(G) Step of Reducing Cysteine Employed for Ligation into Alanine in Fragment (A+B+C+D+E+F) (see FIG. 10).
(H) Step of Deprotecting the Protecting Group of Cysteine (see FIG. 11)
(II) Synthesis of Each Peptide Fragment
(II-1. Synthesis of Peptide Fragment A-SPh)

In the present specification, "—SPh" in peptide fragment A-SPh means a thiophenyl. In other words, peptide fragment A-SPh means having a thiophenyl on the C-terminal of peptide fragment A.

HMPB-PEGA resin (from Merck) (50 μmol) was placed in a solid phase synthesis column, Fmoc-Ala (0.25 mmol), MSNT (0.25 mmol), and N-methyl imidazole (0.27 mmol) were dissolved in DCM (1.25 ml), placed in the solid phase synthesis column, and stirred at 25° C. for 2 hours.

After stirring, the resin was washed with DCM and DMF. The Fmoc group was treated with 20% piperidine/DMF solution (2 ml) for 15 minutes and deprotected. After washing with DMF, subsequent peptide chain elongation was carried out with the method shown below to allow the sequential condensation of amino acids.

Amino acids having the amino group protected with a Fmoc group was dissolved in dimethylformamide (DMF) (1 ml), then HOBt (0.25 mmol) and diisopropylcarbodiimide (DIC) (0.25 mmmol) were added, activated for 5-10 minutes, and this was then added to the solid phase synthesis column. This was reacted at 37 degrees for 15 minutes with a microwave, and the resin was washed with DCM and DMF. This operation was repeated, and amino acids protected with Fmoc and Boc groups (0.25 mmol) were used to sequentially condense amino acids. Note that microwave was not used for amino acids Fmoc-Cys (Trt), Fmoc-Cys (Acm), and Fmoc-His (Trt), but reacted at room temperature for 15 minutes.

As an amino acid having the amino group nitrogen of the amino acid protected with a Fmoc group, Fmoc-Lys(Boc), Fmoc-Ala, Fmoc-Glu(OtBu), Fmoc-Leu, Fmoc-Leu, Fmoc-Tyr(tBu), Fmoc-Arg(Pbf), Fmoc-Glu(OtBu), Fmoc-Leu, Fmoc-Val, Fmoc-Arg(Pbf), Fmoc-Ser(tBu), Fmoc-Asp (OtBu), Fmoc-Cys(Acm), Fmoc-Ile, Fmoc-Leu, Fmoc-Arg (Pbf), Fmoc-Pro, Fmoc-Pro, and Fmoc-Ala were sequentially employed and linked to the solid phase resin. As a result, a 21-residue peptide (3) Ala-Lys(Boc)-Ala-Glu(OtBu)-Leu-Leu-Tyr(tBu)-Arg(Pbf)-Glu(OtBu)-Leu-Val-Arg(Pbf)-Ser(tBu)-Asp(OtBu)-Cys(Acm)-Ile-Leu-Arg(Pbf)-Pro-Pro-Ala-NH₂ (SEQ ID NO:3) was obtained on the solid phase resin.

After washing peptide (3) obtained above with DCM and DMF, a mixed solution of trifluoroethanol and acetic acid (1:1) was added so that the resin was sufficiently soaked, and stirred for 12 hours at room temperature to cleave into the resin and peptide 3. The cleaved resin was filtered off, and the reaction solution was concentrated under reduced pressure. The residue obtained was concentrated, and peptide (3) having the amino acid side chain protected: Ala-Lys(Boc)-Ala-Glu(OtBu)-Leu-Leu-Tyr(tBu)-Arg(Pbf)-Glu(OtBu)-Leu-Val-Arg(Pbf)-Ser(tBu)-Asp(OtBu)-Cys(Acm)-Ile-Leu-Arg (Pbf)-Pro-Pro-Ala-NH₂ (SEQ ID NO:3) was obtained.

Peptide 3 having a 21-residue amino acid and having the amino acid side chain protected was transferred to a 25 mL recovery flask, and dissolved in DMF (2.5 mL). Subsequently, this was cooled under nitrogen atmosphere to −15° C. to −20° C. To this was added thiophenol (10.2 μl, 0.1 mmol), followed by PyBOP (52.0 mg, 0.10 mmol), and then DIPEA (18.0 μl, 0.1 mmol). After stirring at −20° C. for 3 hours, diethyl ether was added to precipitate the peptide. To the residue was added trifluoroacetic acid:water:TIPS (=95: 2.5:2.5), and this was stirred at room temperature. After 2 hours, this solution was added again to a separately prepared diethyl ether to allow precipitation, and then subjected to separation by centrifugation to remove the solution portion, thereby affording a residue containing the target peptide in thioester form. This residue obtained was purified by HPLC [column: Vydac (C18), φ 10×250 nut, flow rate: 4.0 mL/min, eluent solution A: 0.1% TFA-water, solution B: 0.09% TFA/10% water/90% AN gradient A:B=75:25->25:75 (30 minutes) linear gradient] to afford peptide fragment A-SPh (4) (SEQ ID NO:4): H₂N-Ala-Pro-Pro-Arg-Leu-Ile-Cys(Acm)-Asp-Ser-Arg-Val-Leu-Glu-Arg-Tyr-Leu-Leu-Glu-Ala-Lys-Ala-SPh having a thiophenyl ester at the C-terminal. ESI-MS: m/z calcd. for $C_{116}H_{190}N_{32}O_{30}S_2$: $[M+2H]^{2+}$ 1289.5, $[M+3H]^{3+}$ 860.0 $[M+4H]^{4+}$ 645.3. found for $[M+2H]^{2+}$ 1289.3 $[M+3H]^{3+}$ 860.0, $[M+4H]^{4+}$ 645.3.

(II-2. Synthesis of Peptide Fragment B-SBn)

Peptide fragment B-SBn was synthesized under a condition similar to the method for synthesizing the above II-1. peptide fragment A-SPh using the Fmoc solid phase synthesis method.

As an amino acid protected with Fmoc and BoC groups, Fmoc-Tyr(tBu), Fmoc-Phe, Fmoc-Asn(Trt), Fmoc-Val, Fmoc-Lys(Boc), Fmoc-Thr(tBu), Fmoc-Asp(OtBu), Fmoc-Pro, Fmoc-Val, Fmoc-Thr(tBu), Fmoc-Ile, Fmoc-Asn(Trt), Fmoc-Glu(OtBu), Fmoc-Asn(Trt), Fmoc-Leu, Fmoc-Ser (tBu), Fmoc-Cys(Acm), Fmoc-His(Trt), Fmoc-Glu(OtBu), Fmoc-Ala, Fmoc-Cys(Acm), Fmoc-Gly, Fmoc-Thr(tBu), Fmoc-Thr(tBu), Fmoc-Ile, Fmoc-Asn(Trt), Fmoc-Gln(Trt), and Fmoc-Cys(Trt) were sequentially employed and linked to the solid phase resin. As a result, a 28-residue peptide (5) Tyr (tBu)-Phe-Asn (Trt)-Val-Lys (Boc)-Thr (tBu)-Asp(OtBu)-Pro-Val-Thr(tBu)-Ile-Asn(Trt)-Glu(OtBu)-Asn(Trt)-Leu-Ser(tBu)-Cys(Acm)-His(Trt)-Glu(OtBu)-Ala-Cys(Acm)-Gly-Thr(tBu)-Thr(tBu)-Ile-Asn(Trt)-Gln(Trt)-Cys(Trt)-NH₂ (SEQ ID NO:5) was obtained on the solid phase resin.

Peptide (5) obtained above was processed under a condition similar to the method for synthesizing the above II-1. peptide fragment A-SPh to cleave off from the resin, and peptide (5): Tyr(tBu)-Phe-Asn(Trt)-Val-Lys(Boc)-Thr(tBu)-Asp(OtBu)-Pro-Val-Thr(tBu)-Ile-Asn(Trt)-Glu(OtBu)-Asn (Trt)-Leu-Ser(tBu)-Cys(Acm)-His(Trt)-Glu(OtBu)-Ala-Cys (Acm)-Gly-Thr(tBu)-Thr(tBu)-Ile-Asn(Trt)-Gln(Trt)-Cys (Trt)-NH₂ (SEQ ID NO:5) having the amino acid side chain protected was obtained.

Peptide (5) having a 28-residue peptide amino acid and having the amino acid side chain protected was transferred to a 25 mL recovery flask, and dissolved in DMF (2.5 mL). Subsequently, this was cooled under nitrogen atmosphere to −15° C. to −20° C. To this was added benzyl mercaptan (11.7 μl, 0.1 mmol), followed by PyBOP (52.0 mg, 0.10 mol), and then DIPEA (18.0 μl, 0.1 mmol). After stirring at −20° C. for 3 hours, diethyl ether was added to precipitate the peptide. To the residue was added trifluoroacetic acid:water:TIPS (=95:

2.5:2.5), and this was stirred at room temperature. After 2 hours, this solution was added again to a separately prepared diethyl ether to allow precipitation, and then subjected to separation by centrifugation to remove the solution portion, thereby affording a residue containing the target peptide in thioester form. This residue obtained was purified by HPLC [column: Vydac (C18), φ 10×250 mm, flow rate: 4.0 mL/min, eluent solution A: 0.1% TFA-water, solution B: 0.09% TFA/10% water/90% AN gradient A:B=70:30->20:80 (30 minutes) liner gradient] to afford peptide fragment B-SBn (6) (SEQ ID NO:6): $H_2$N-Cys-Gln-Asn-Ile-Thr-Thr-Gly-Cys(Acm)-Ala-Glu-His-Cys(Acm)-Ser-Leu-Asn-Glu-Asn-Ile-Thr-Val-Pro-Asp-Thr-Lys-Val-Asn-Phe-Tyr-SBn having a thiobenzyl ester at the C-terminal.

ESI-MS: m/z calcd. for $C_{144}H_{219}N_{37}O_{48}S_4$: $[M+2H]^{2+}$ 1863.4, $[M+3H]^{3+}$ 1122.6, $[M+4H]^{4+}$ 842.2. found for $[M+2H]^{2+}$ 1863.4, $[M+3H]^{3+}$ 1122.6, $[M+4H]^{4+}$ 842.2.

(II-3. Synthesis of Peptide Fragment C—SR)

Solid phase synthesis was carried out with a Prostyrene column (Tokyo Rika, No. 183 470). Amino-PEGA resin (50 μmol, 1.67 g) was placed in a Prostyrene column, and sufficiently conditioned with DMF solvent. Subsequently, a solution of S-trityl-3-mercaptopropionic acid (200 μmol), HBTU (190 μmol), and DIPEA (800 μmol) dissolved in DMF was added to the amino-PEGA resin, and this was stirred at ordinary temperature. After 30 minutes, the resin was washed with DMF and DCM, and 95% TFA and 5% TIPS were added. After 2 minutes, the solution was filtered, TFA and TIPS were added again, and after 2 minutes, the resin was washed with DMF. To this resin, a mixed solution of Boc-Ala (200 mM), HBTU (190 mM), and DIPEA (400 mM) dissolved in DMF was added to the resin to allow the condensation of the first amino acid residue alanine. After 20 minutes, the resin was successively washed with DMF and dioxane. To this resin, 10% sulfuric acid/dioxane solution was added, filtered after 5 minutes, the same solution was further added, and stirred for 30 minutes to carry out the deprotection of the Boc group. Subsequently, this operation was repeated using amino acids protected with a Boc group to sequentially condense amino acids.

As an amino acid protected with a Boc group, Boc-Gly, Boc-Arg(di-Z), Boc-Leu, Boc-Val, Boc-Ala, Boc-Glu(Bn), Boc-Ser(Bn), Boc-Leu, Boc-Leu, Boc-Ala, Boc-Leu, Boc-Gly, Boc-Gln, Boc-Trp(CHO), Boc-Val, Boc-Glu(Bn), Boc-Val, Boc-Ala, Boc-Gln, Boc-Gln, Boc-Gly, Boc-Val, Boc-Glu(Bn), Boc-Met, Boc-Arg(di-Z), Boc-Lys(Cl—Z), Boc-Trp(CHO), and Boc-Thz were sequentially employed and linked to the solid phase resin. As a result, a 29-residue peptide (7) Ala-Gly-Arg(di-Z)-Leu-Val-Ala-Glu(Bn)-Ser(Bn)-Leu-Leu-Ala-Leu-Gly-Gln-Trp(CHO)-Val-Glu(Bn)-Val-Ala-Gln-Gln-Gly-Val-Glu(Bn)-Met-Arg(di-Z)-Lys(Cl—Z)-Trp(CHO)-Thz-NH (SEQ ID NO:7) was obtained on the solid phase resin.

After washing peptide (7) on the resin obtained above with DCM, a cocktail cooled to 0° C. comprising TFA (400 μL), TfOH (40 μL), EDT (20 μL), and thioanisole (40 μL) was added, and stirred at 0° C. After 30 minutes, the solution was filtered, the resin was washed with TFA, diethyl ether, DMF, DCM, and TFA in this order, the same amount of the above cocktail was added again, and stirred at 0° C. After 30 minutes, the solution was filtered, and the resin was washed well with TFA, diethyl ether, and DMF in this order. MESNa (5 mg) was dissolved in 200 mM phosphate buffer (95 μL) containing 6 M guanidine hydrochloride, and added to this resin. After 12 hours, an eluate solution containing the target peptide in thioester form was obtained. This solution obtained was purified by HPLC to afford peptide fragment C—SR (8) (SEQ ID NO:8): HN-Thz-Trp-Lys-Arg-Met-Glu-Val-Gly-Gln-Gln-Ala-Val-Glu-Val-Trp-Gln-Gly-Leu-Ala-Leu-Leu-Ser-Glu-Ala-Val-Leu-Arg-Gly-Ala-SR having a thioester at the C-terminal. Note that —SR indicates a sulfonic acid ethyl thioester.

ESI-MS: m/z calcd. for $C_{145}H_{235}N_{41}O_{42}S_4$: $[M+2H]^{2+}$ 1677.5, $[M+3H]^{3+}$ 1118.6, $[M+4H]^{4+}$ 839.2. found for $[M+2E]^{2+}$ 1677.5, $[M+3H]^{3+}$ 1118.6, $[M+4H]^{4+}$ 839.2.

(II-4. Synthesis of Glycopeptide Fragment D-SR Having Sialic Acid Sugar Chain)

Similarly to the method for synthesizing the above II-3. peptide fragment C-SR, using the solid phase synthesis method by Boc method, amino acids were sequentially condensed using amino acids protected with a Boc group up to the serine residue of the amino acid.

As an amino acid protected with a Boc group, Boc-Lys(Cl—Z), Boc-Asp(Bn), Boc-Val, Boc-His(DNP), Boc-Leu, Boc-Gln, Boc-Leu, Boc-Pro, Boc-Glu(Bn), Boc-Trp(CHO), Boc-Pro, Boc-Gln, Boc-Ser(Bn), and Boc-Ser(Bn) were sequentially employed and linked to the solid phase resin. As a result, peptide fragment (9) Lys(Cl—Z)-Asp(Bn)-Val-His(DNP)-Leu-Gln-Leu-Pro-Glu(Bn)-Trp(CHO)-Pro-Gln-Ser(Bn)-Ser(Bn) (SEQ ID NO:9) was obtained on the solid phase resin.

To peptide fragment (9) obtained above, 10% sulfuric acid/dioxane solution was added, filtered after 5 minutes, the same solution was further added, and stirred for 30 minutes to carry out the deprotection of the Boc group. Subsequently, this was washed with DMF, and 5% DIPEA/DMF was added. After 1 minute, this was washed well with DMF, and a solution of Boc-diphenacyl-disialoglycoasparagine (4 μmol), DEPBT (6 μmol), and DIPEA (4 μmol) dissolved in DMF was added, and stirred at ordinary temperature. After 14 hours, the resin was washed well with DMF. Condensation of sugar chain was carried out again under the above condition. In doing so, condensation was carried out with a method similar to the above at an amino acid concentration of 40 mM in order to prevent side reactions of the sugar chain hydroxyl group. As amino acids protected with a Boc group, Boc-Val, Boc-Leu, Boc-Leu, and Boc-Thz were sequentially employed and linked to the solid phase resin. As a result, a 19-residue glycopeptide (10) Lys(Cl—Z)-Asp(Bn)-Val-His(DNP)-Leu-Gln-Leu-Pro-Glu(Bn)-Trp(CHO)-Pro-Gln-Ser(Bn)-Ser(Bn)-Asn(diphenacyl-disialo sugar chain)-Val-Leu-Leu-Thz-NH (SEQ ID NO:10) was obtained on the solid phase resin.

After washing peptide (10) on the resin obtained above with DCM, a cocktail cooled to 0° C. comprising TFA (350 μL), DMS (210 μL), m-cresol (70 μL), and TfOH (70 μL) was added, and stirred at 0° C. After 30 minutes, the solution was filtered, the resin was washed with TFA, diethyl ether, DMF, DCM, and TFA in this order, the same amount of the above cocktail was added again, and stirred at 0° C. After 30 minutes, the solution was filtered, the resin was washed with TFA, diethyl ether, DMF, DCM, and TFA in this order, the same amount of the above cocktail was added again, and stirred at 0° C. After 2 hours, the solution was filtered, and the resin was washed well with TFA, diethyl ether, and DMF in this order. MESNa (5 mg) was dissolved in 200 mM phosphate buffer (95 μL) containing 6 M guanidine hydrochloride, and added to this resin. After 12 hours, an eluate solution containing the target peptide in thioester form was obtained. This was purified by HPLC to afford peptide fragment D-SR (11) (SEQ ID NO:11): HN-Thz-Leu-Leu-Val-Asn(diphenacyl-disialo sugar chain)-Ser-Ser-Gln-Pro-Trp(CHO)-Glu-Pro-Leu-Gln-Leu-His-Val-Asp-Lys-SR having a thioester at the C-terminal. Note that —SR indicates a sulfonic acid ethyl thioester.

ESI-MS: m/z calcd. for $C_{203}H_{306}N_{32}O_{95}S_3$: $[M+3H]^{3+}$ 1604.7, $[M+4H]^{4+}$ 1203.7, $[M+5H]^{5+}$ 963.1. found for $[M+3H]^{3+}$ 1605.4, $[M+4H]^{4+}$ 1204.3, $[M+5H]^{5+}$ 963.2.

(II-5. Synthesis of Peptide Fragment E-SR)

Peptide fragment E-SR was synthesized under a condition similar to the method for synthesizing the above II-3. peptide fragment C-SR using the Boc solid phase synthesis method. First, amino acids protected with a Boc group were used up to the serine residue which will be immediately before the glycosylated amino acid link, and amino acids were sequentially condensation from the C-terminal side.

As amino acids protected with a Boc group, Boc-Ala, Boc-Ser(Bn), Boc-Ala, Boc-Ala, Boc-Asp(Bn), Boc-Pro, Boo-Pro, Boc-Ser(Bn), Boc-Ile, Boc-Ala, Boc-Glu(Bn), Boc-Lys(Cl—Z), Boc-Glu(Bn), Boc-Ala, Boc-Gly, Boc-Leu, Boc-Ala, Boc-Arg(di-Z), Boc-Leu, Boc-Leu, Boc-Thr(Bn), Boc-Thr(Bn), Boc-Leu, Boc-Ser(Bn), Boc-Arg(di-Z), Boc-Leu, Boc-Gly, Boc-Ser(Bn), Boc-Val, and Boc-Thz were sequentially employed and linked to the solid phase resin. As a result, a 30-residue peptide (12) Ala-Ser(Bn)-Ala-Ala-Asp(Bn)-Pro-Pro-Ser(Bn)-Ile-Ala-Glu(Bn)-Lys(Cl—Z)-Glu(Bn)-Ala-Gly-Leu-Ala-Arg(di-Z)-Leu-Leu-Thr(Bn)-Thr(Bn)-Leu-Ser(Bn)-Arg(di-Z)-Leu-Gly-Ser(Bn)-Val-Thz-NH (SEQ ID NO:12) was obtained on the solid phase resin.

Peptide (12) on the resin obtained above is processed under a condition similar to the method for synthesizing the above II-3. peptide fragment C-SR to cleave out from the resin. This was purified by HPLC to afford peptide fragment E-SPh (13) (SEQ ID NO:13): HN-Thz-Val-Ser-Gly-Leu-Arg-Ser-Leu-Thr-Thr-Leu-Leu-Arg-Ala-Leu-Gly-Ala-Glu-Lys-Glu-Ala-Ile-Ser-Pro-Pro-Asp-Ala-Ala-Ser-Ala-SPh having a thioester at the C-terminal. Note that —SR indicates a sulfonic acid ethyl thioester.

ESI-MS: m/z calcd for $C_{131}H_{226}N_{38}O_{44}S_3$: $[M+2H]^{2+}$ 1567.8, $[M+3H]^{3+}$ 1045.5. found for $[M+2H]^{2+}$ 1568.0, $[M+3H]^{3+}$ 1045.6.

(II-6. Synthesis of Peptide Fragment F—OH)

Peptide fragment F—OH was synthesized under a condition similar to the method for synthesizing the above II-1. peptide fragment A-SPh using the Fmoc solid phase synthesis method.

As amino acids protected with a Fmoc group, Fmoc-Arg(Pbf), Fmoc-Asp(OtBu), Fmoc-Gly, Fmoc-Thr(tBu), Fmoc-Arg(Pbf), Fmoc-Cys(Acm), Fmoc-Ala, Fmoc-Glu(OtBu), Fmoc-Gly, Fmoc-Thr(tBu), Fmoc-Tyr(tBu), Fmoc-Leu, Fmoc-Lys(Boc), Fmoc-Leu, Fmoc-Lys(Boc), Fmoc-Gly, Fmoc-Arg(Pbf), Fmoc-Leu, Fmoc-Phe, Fmoc-Asn(Trt), Fmoc-Ser(tBu), Fmoc-Tyr(tBu), Fmoc-Val, Fmoc-Arg(Pbf), Fmoc-Phe, Fmoc-Leu, Fmoc-Lys(Boc), Fmoc-Arg(Pbf), Fmoc-Phe, Fmoc-Thr(tBu), Fmoc-Asp(OtBu), Fmoc-Ala, Fmoc-Thr(tBu), Fmoc-Ile, Fmoc-Thr(tBu), Fmoc-Arg(Pbf), Fmoc-Leu, Fmoc-Pro, and Fmoc-Cys(Trt) were sequentially employed and linked to the solid phase resin. As a result, a 39-residue peptide (14) Arg(Pbf)-Asp(OtBu)-Gly-Thr(tBu)-Arg(Pbf)-Cys(Acm)-Ala-Glu(OtBu)-Gly-Thr(tBu)-Tyr(tBu)-Leu-Lys(Boc)-Leu-Lys(Boc)-Gly-Arg(Pbf)-Leu-Phe-Asn(Trt)-Ser(tBu)-Tyr(tBu)-Val-Arg(Pbf)-Phe-Leu-Lys(Boc)-Arg(Pbf)-Phe-Thr(tBu)-Asp(OtBu)-Ala-Thr(tBu)-Ile-Thr(tBu)-Arg(Pbf)-Leu-Pro-Cys(Trt)-NH$_2$ (SEQ ID NO:14) was obtained on the solid phase resin.

Peptide (14) on the resin obtained above was cleaved out from the resin with a method generally employed with the Fmoc method and purified by HPLC to afford peptide fragment F (15) (SEQ ID NO:15): H$_2$N-Cys-Pro-Leu-Arg-Thr-Ile-Thr-Ala-Asp-Thr-Phe-Arg-Lys-Leu-Phe-Arg-Val-Tyr-Ser-Asn-Phe-Leu-Arg-Gly-Lys-Leu-Lys-Leu-Tyr-Thr-Gly-Glu-Ala-Cys(Acm)-Arg-Thr-Gly-Asp-Arg.

ESI-MS: m/z calcd for $C_{206}H_{334}N_{62}O_{56}S_2$: $[M+3H]^{3+}$ 1547.5, $[M+4H]^{4+}$ 1160.8, $[M+5H]^{5+}$ 928.9, $[M+6H]^{6+}$ 774.2, $[M+7H]^{7+}$ 663.8. found for $[M+3H]^{3+}$ 1547.2, $[M+4H]^{4+}$ 1160.8, $[M+5H]^{5+}$ 928.9, $[M+6H]^{6+}$ 774.2, $[M+7H]^{7+}$ 663.8.

(III) Synthesis of Disialoglycosylated Erythropoietin by Linking of Each Fragment The linking of each fragment produced above and the synthesis of disialoglycosylated erythropoietin were carried out in a total of 10 steps shown below.

(III-1. Step 1: Linking of Peptide Fragment E and Peptide Fragment F)

The two fragment types of a 30-residue peptide fragment E (13) having a thiophenyl ester form at the C-terminal (3.7 mg) and a 39-residue peptide fragment F (15) (2.5 mg) were placed in the same recovery flask. After dissolving in a buffer solution at pH 6.8 (0.40 ml) (prepared with 6 M guanidine hydrochloride solution, 0.2 M phosphate solution, and 20 mM tris-carboxyethyl phosphine solution (TCEP solution)), MPAA (2.7 mg) was added and reacted at room temperature. After 3 hours, the reaction was confirmed by HPLC, then a methoxyamine solution was added to the reaction solution, adjusted to pH 4.0, and reacted at room temperature to thereby convert the N-terminal thiazolidine-type cysteine into cysteine. After 2 hours, the production of the target object was confirmed with HPLC and ESI-MS. The reaction solution was purified by HPLC [column: Vydac (C18), φ 10×250 mm, flow rate: 4.0 mL/min, eluent solution A: 0.1% TFA-water solution B: 0.09% TFA/10% water/90% AN, A:B=75:25->25:75(30 minutes) linear gradient] to obtain the target peptide fragment (E+F) (16) (SEQ ID NO:16) (FIG. 6).

ESI-MS: m/z calcd for $C_{334}H_{554}N_{100}O_{97}S_3$: $[M+4H]^{4+}$ 1905.7, $[M+5H]^{5+}$ 1524.8, $[M+6H]^{6+}$ 1270.8, $[M+7H]^{7+}$ 1089.4, $[M+8H]^{8+}$ 953.4, $[M+9H]^{9+}$ 847.5, $[M+10H]^{10+}$ 762.9. found for 1906.0, 1525.0, 1271.0, 1089.7, 953.7, 847.8, 763.2.

(III-2. Step 2: Linking of Peptide Fragment D and Peptide Fragment (E+F))

Figure 7:
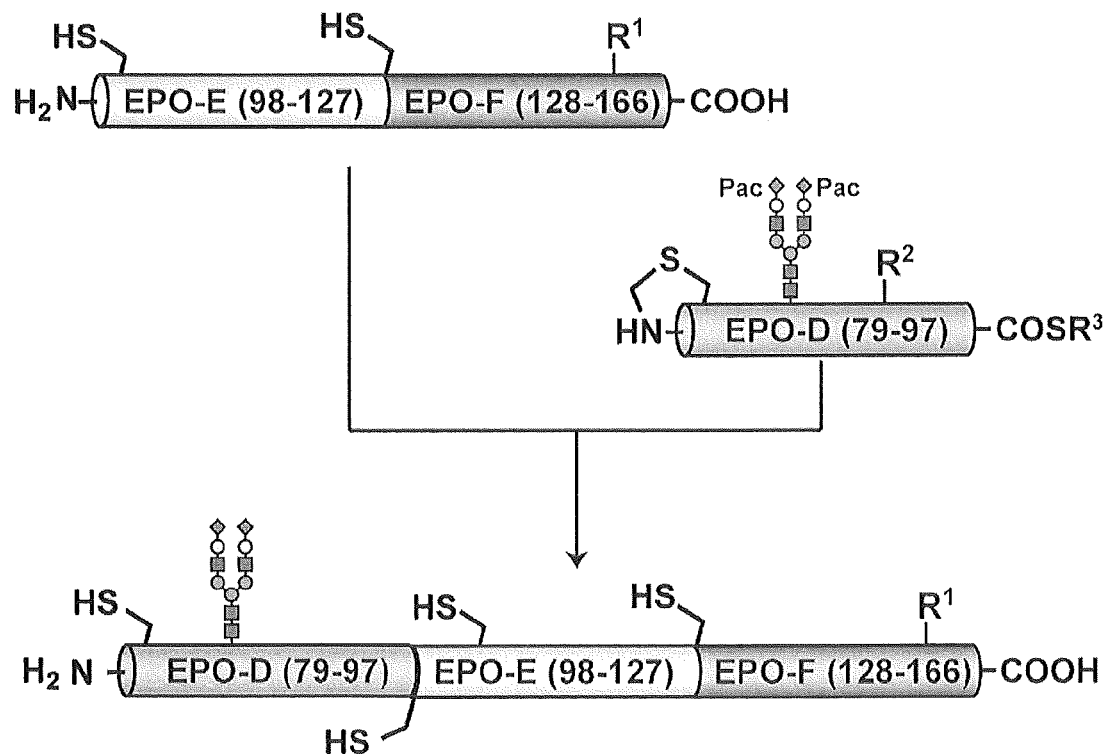
FIG. 7 is a schematic diagram showing one embodiment of the present invention, which is a part of a step of a method for manufacturing an amino acid sequence having a biantennary disialoglycoasparagine using erythropoietin as the model peptide. Specifically, it is a schematic diagram showing the step of linking fragment (E+F) having the amino acid sequence of amino acid sequences 98-166 of erythropoietin with fragment D having the amino acid sequence of amino acid sequences 79-97 of erythropoietin to produce fragment (D+E+F), the step of converting the N-terminal thiazolidine-type cysteine of fragment (D+E+F) into cysteine, and the step of removing the phenacyl group on the sugar chain sialic acid and the formyl group (CHO) which is the Trp protecting group.

The two fragment types of a 19-residue disialoglycosylated peptide fragment D (11) having a thioester form at the C-terminal (3.8 mg) and peptide fragment (E+F) obtained in the above Step 1 (16) (6.0 mg) were placed in the same recovery flask, and dissolved in a buffer solution at pH 6.8 (0.40 ml) (prepared with 6 M guanidine hydrochloride solution, 0.2 M phosphate solution, and 40 mM TCEP solution). Subsequently, MPAA (2.7 mg) was added and reacted at room temperature. After confirming the completion of the reaction with HPLC and ESI-MS, 2-mercapto ethanol (3.0 µL) (0.2 M phosphate solution, pH 8.0, added to 60 µL and adjusted) was added and reacted at room temperature to thereby deprotect phenacyl and formyl groups. After 2 hours, this was neutralized with hydrochloric acid, and then a methoxyamine solution was added to the reaction solution, adjusted to pH 4.0, and reacted at room temperature to thereby convert the thiazolidine-type cysteine into cysteine. After 3 hours, the production of the target object was confirmed with HPLC and ESI-MS. The reaction solution was purified by HPLC [column: Vydac (C18), φ 10×250 mm, flow rate: 4.0 mL/min, eluent solution A: 0.1% TFA-water solution B: 0.09% TFA/10% water/90% AN, A:B=75:25->25:75 (30 minutes) liner gradient] to obtain the target glycosylated polypeptide fragment (D+E+F) (17) (SEQ ID NO:17) (FIG. 7).

ESI-MS: m/z calcd. for $C_{517}H_{842}N_{132}O_{186}S_4$ $[M+7H]^{7+}$ 1716.9, $[M+8H]^{8+}$ 1502.4, $[M+9H]^{9+}$ 1335.6, $[M+10H]^{10+}$ 1202.1, $[M+11H]^{11+}$ 1092.9, $[M+12H]^{12+}$ 1001.9,

[M+13H]$^{13+}$ 924.9, [M+14H]$^{14+}$ 859.0. found 1717.2, 1502.8, 1335.9, 1202.4, 1093.3, 1002.2, 925.1, 858.7.

(III-3. Step 3: Linking of Peptide Fragment C and Glycosylated Peptide Fragment (D+E+F))

Figure 8:
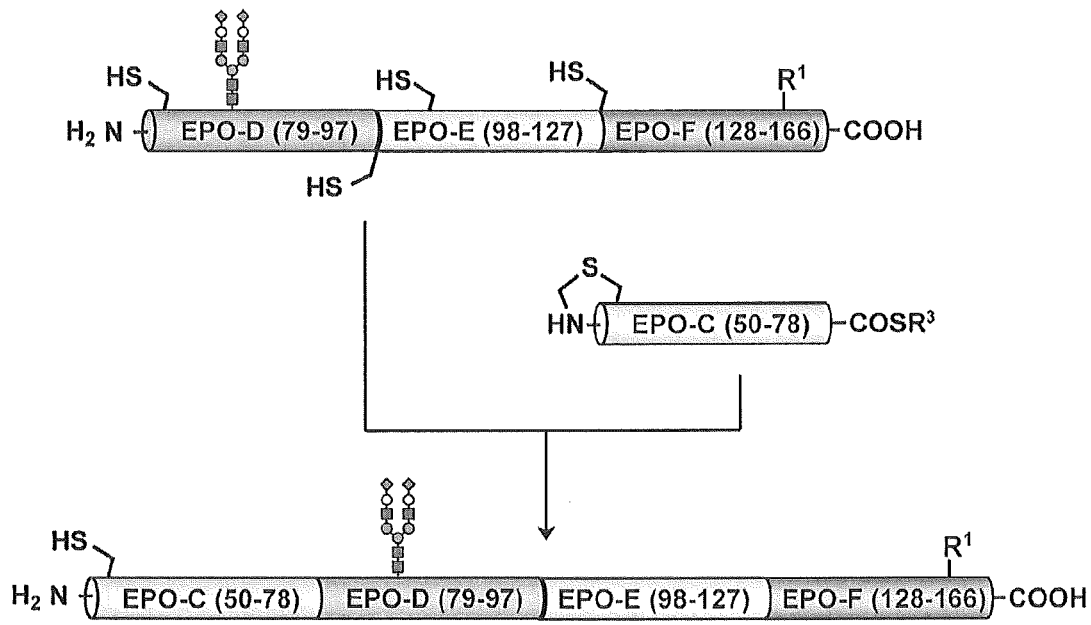
FIG. 8 is a schematic diagram showing one embodiment of the present invention, which is a part of a step of a method for manufacturing an amino acid sequence having a biantennary disialoglycoasparagine using erythropoietin as the model peptide. Specifically, it is a schematic diagram showing the step of linking fragment (D+E+F) having the amino acid sequence of amino acid sequences 79-166 of erythropoietin with fragment C having the amino acid sequence of amino acid sequences 50-78 of erythropoietin to produce fragment (C+D+E+F), the step of reducing the cysteine employed for ligation into alanine, and the step of converting the N-terminal thiazolidine-type cysteine of fragment (C+D+E+F) into cysteine.

The two fragment types of a 29-residue peptide fragment C (8) having a thioester form at the C-terminal (1.34 mg) and glycosylated polypeptide fragment (D+E+F) obtained in the above Step 2 (17) (4.8 mg) were placed in the same recovery flask, and dissolved in a buffer solution at pH 6.8 (0.40 ml) (prepared with 6 M guanidine hydrochloride solution, 0.2 M phosphate solution, and 40 mM TCEP solution). Subsequently, MPAA (1.4 mg) was added and reacted at room temperature. After confirming the production of the target object with HPLC and ESI-MS, the reaction solution was purified by HPLC [column: Vydac (C18), φ 10×250 μm, flow rate: 4.0 mL/min, eluent solution A: 0.1% TFA-water solution B: 0.09% TFA/10% water/90% AN, A:B=70:30->20:80 (30 minutes) liner gradient] to obtain the target glycosylated polypeptide fragment (C+D+E+F) (18) (SEQ ID NO:18) (FIG. 8).

ESI-MS: m/z calcd. for C$_{661}$H$_{1071}$N$_{173}$O$_{235}$S$_6$: [M+8H]$^{8+}$ 1905. [M+9H]$^{9+}$ 1693.7, [M+10H]$^{10+}$ 1524.4, [M+11H]$^{11+}$ 1385.9, [M+12H]$^{12+}$ 1270.5, [M+13H]$^{13+}$ 1172.9, [M+14H]$^{14+}$ 1089.1, [M+15H]$^{15+}$ 1016.6, [M+16H]$^{16+}$ 953.1, [M+17H]$^{17+}$ 897.1. found 1905.1, 1693.8, 1524.5, 1385.9, 1270.7, 1173.0, 1089.2, 1016.7, 953.2, 897.2.

(III-4. Step 4: Reduction of Cys into Ala)

A 117-residue glycosylated peptide fragment (C+D+E+F) (18) having a free thiol group at Cys at positions corresponding to positions 79, 98, and 128 in the amino acid sequence of erythropoietin and having a disialo sugar chain on Asn at a position corresponding to position 83 in the amino acid sequence of erythropoietin obtained in the above Step 3 (3.8 mg) was placed in a recovery flask. After dissolving in a buffer solution at pH 7.0 (1.0 ml) (prepared with 6 M guanidine hydrochloride solution and 0.2 M phosphate solution), tris-ethylcarboxy phosphine (TCEP) at pH 7.0 (130 mg), MESNa (50 mg), and VA-044 (1.6 mg) were added and reacted at room temperature. After 10 hours, the production of the target object was confirmed with HPLC and ESI-MS. The reaction solution was purified by HPLC [column: Vydac (C18), φ 10×250 mm, flow rate: 4.0 mL/min, eluent solution A: 0.1% TFA-water solution B: 0.09% TFA/10% water/90% AN, A:B=70:30->20:80 (30 minutes) liner gradient] to obtain the target glycosylated peptide fragment (C+D+E+F) (19) (SEQ ID NO:19) (FIG. 8).

ESI-MS: m/z calcd. for C$_{661}$H$_{1071}$N$_{173}$O$_{225}$S$_3$: [M+9H]$^{9+}$ 1683.9, [M+10H]$^{10+}$ 1514.8, [M+11H]$^{11+}$ 1377.2, [M+12H]$^{12+}$ 1262.5, [M+13H]$^{13+}$ 1165.5, [M+14H]$^{14+}$ 1082.3, [M+15H]$^{15+}$ 1010.2, [M+16H]$^{16+}$ 947.1, [M+17H]$^{17+}$ 891.5, [M+18H]$^{18+}$ 842.0. found 1683.1, 1514.9, 1377.2, 1262.7, 1165.6, 1082.3, 1010.3, 947.2, 891.6, 842.1.

(III-5. Step 5: De-Thz Reaction)

After dissolving a 117-residue glycosylated polypeptide (C+D+E+F) (19) having a disialo sugar chain on Asn at a position corresponding to position 83 in the amino acid sequence of erythropoietin obtained in the above Step 4 (2.0 mg) in a buffer solution at pH 6.8 (0.05 ml) (prepared with 0.2 M phosphate solution), 0.2 M methoxyamine solution was added to the reaction solution, adjusted to pH 4.0, and reacted at room temperature. After 3 hours, the reaction solution was purified by HPLC [column: Vydac (C18), φ 10×250 mm, flow rate: 4.0 mL/min, eluent solution A: 0.1% TFA-water solution B: 0.09% TFA/10% water/90% AN, A:B=75:25->30:70 (30 minutes) liner gradient] to obtain the target glycosylated peptide fragment (C+D+E+F) (20) (SEQ ID NO:20) (FIG. 8).

ESI-MS: m/z calcd. for C$_{660}$H$_{1071}$N$_{173}$O$_{225}$S$_3$: [M+9H]$^{9+}$ 1681.6, [M+10H]$^{10+}$ 1513.6, [M+11H]$^{11+}$ 1376.0, [M+12H]$^{12+}$ 1261.5, [M+13H]$^{13+}$ 1164.5, [M+14H]$^{14+}$ 1081.4, [M+15H]$^{15+}$ 1009.4, [M+16H]$^{16+}$ 946.4, [M+17H]$^{17+}$ 890.8[M+18H] 841.3. found 1681.6, 1513.6, 1376.0, 1261.4, 1164.4, 1081.3, 1009.4, 946.3, 890.7, $41.3.

(III-6. Step 6: Linking of Peptide Fragment A and Peptide Fragment B)

The two fragment types of a 21-residue peptide fragment A (4) having a thiophenyl ester form at the C-terminal (2.0 mg) and a 28-residue peptide fragment B (6) (2.7 mg) were placed in the same recovery flask, dissolved in a buffer solution at pH 6.5 (0.40 ml) (prepared with 6 M guanidine hydrochloride solution, 0.2 M phosphate solution, and 30 mM tris-carboxyethyl phosphine solution (TCEP solution)), and reacted at room temperature. After the completion of the reaction, MESNa (5.2 mg) was added and reacted at room temperature. After 2 hours, the production of the target object was confirmed with HPLC and ESI-MS. The reaction solution was purified by HPLC [column: Vydac (C18), φ 10×250 mm, flow rate: 4.0 mL/min, eluent solution A: 0.1% TFA-water solution B: 0.09% TFA/10% water/90% AN, A:B=65:35->15:85(30 minutes) liner gradient] to obtain the target peptide fragment (A+B) (21) (SEQ ID NO:21) (FIG. 5).

ESI-MS: m/z calcd. for C$_{249}$H$_{401}$N$_{69}$O$_{81}$S$_6$: [M+3H]$^{3+}$ 1950.1, [M+4H]$^{4+}$ 1463.4, [M+5H]$^{5+}$ 1170.9, [M+6H]$^{6+}$ 975.9, [M+7H]$^{7+}$ 836.7. found 1950.7, 1463.6, 1171.1, 976.1, 836.8.

(III-7. Step 7: Linking of Peptide Fragment (A+B) and Glycosylated Peptide Fragment (C+D+E+F))

The two fragment types of peptide fragment (A+B) (21) having a thioester form at the C-terminal of residue 49 obtained in the above Step 6 (2.0 mg) and glycosylated polypeptide fragment (C+D+E+F) (20) obtained in the above Step 5 (3.5 mg) were placed in the same recovery flask. After dissolving in a buffer solution at pH 7.0 (0.077 ml) (prepared with 6 M guanidine hydrochloride solution, 0.2 M phosphate solution, and 50 mM TCEP solution), MPAA (ca. 0.8 mg) was added and reacted at room temperature. After confirming the production of the target object with HPLC and ESI-MS, the reaction solution was purified by HPLC [column: Vydac (C18), φ 10×250 mm, flow rate: 1.0 mL/min, eluent solution A: 0.1% TFA-water solution B: 0.09% TFA/10% water/90% AN, A:B=65:35->25:75(30 minutes) liner gradient] to obtain the target glycosylated peptide fragment (A+B+C+D+E+F) (22) (SEQ ID NO:22) (FIG. 9).

ESI-MS: m/z calcd. for C$_{907}$H$_{1468}$N$_{242}$O$_{303}$S$_7$: [M+11H]$^{11+}$ 1895.1, [M+12H]$^{12+}$ 1737.3, [M+13H]$^{13+}$ 1603.7, [M+14H]$^{14+}$ 1489.2, [M+15H]$^{15+}$ 1390.0, [M+16H]$^{16+}$ 1303.2, [M+17H]$^{17+}$ 1226.6, [M+18H]$^{18+}$ 1158.5, [M+19H]$^{19+}$ 1097.6, [M+20H]$^{20+}$ 1042.8, [M+21H]$^{21+}$ 993.2, [M+22H]$^{22+}$ 948.1, [M+23H]$^{23+}$ 906.9, [M+24H]$^{24+}$ 869.1, [M+25H]$^{25+}$ 834.4. found 1895.0, 1737.3, 1603.8, 1489.1, 1389.9, 1303.2, 1226.6, 1158.5, 1097.7, 1042.7, 993.2, 948.0, 906.9, 869.2, 834.4.

(III-8. Step 8: Reduction of Cys into Ala)

A 166-residue glycosylated polypeptide (A+B+C+D+E+F) (22) having a free thiol group at Cys at positions 22 and 50 and having a disialo sugar chain on Asn at position 83 obtained in the above Step 7 (1.0 mg) was placed in a recovery flask. After dissolving in a buffer solution at pH 7.0 (0.2 ml) (prepared with 6 M guanidine hydrochloride solution and 0.2 M phosphate solution), tris-ethylcarboxy phosphine (TCEP) at pH 7.0 (26 mg), MESNa (10 mg), and VA-044 (0.32 mg) were added and reacted at room temperature. After 4 hours, the production of the target object was confirmed with HPLC and ESI-MS. The reaction solution was purified by HPLC

[column: Vydac (C8), φ 10×250 mm, flow rate: 4.0 mL/min, eluent solution A: 0.1% TFA-water solution B: 0.09% TFA/ 10% water/90% AN, A:B=70:30->20:80 (30 minutes) liner gradient] to obtain the target glycosylated polypeptide fragment (A+B+C+D+E+F) (23) (SEQ ID NO:23) (FIG. 10).

ESI-MS: m/z calcd. for $C_{907}H_{1468}N_{242}O_{303}S_5$: $[M+13H]^{13+}$ 1598.8, $[M+14H]^{14+}$ 1484.7, $[M+15H]^{15+}$ 1385.7, $[M+16H]^{15+}$ 1229.2, $[M+17H]^{17+}$ 1222.8, $[M+18H]^{18+}$ 1155.0, $[M+19H]^{19+}$ 1094.2, $[M+20H]^{20+}$ 1039.6, $[M+21H]^{21+}$ 990.1, $[M+22H]^{22+}$ 945.1, $[M+23H]^{23+}$ 904.1, $[M+24H]^{21+}$ 866.5, $[M+25H]^{25+}$ 831.9, $[M+26H]^{26+}$ 799.9, $[M+27H]^{27+}$ 770.3. found 1598.6, 1484.4, 1385.5, 1299.0, 1222.7, 1154.9, 1094.1, 1039.4, 990, 945.2, 904.0, 866.4, 831.6, 799.9, 770.3.

(III-9. Step 9: Deprotection of Acm Group)

Figure 11:
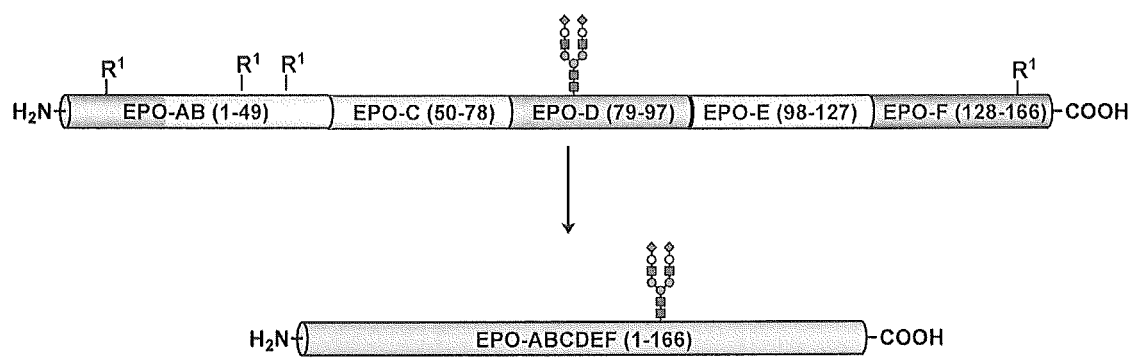
FIG. 11 is a schematic diagram showing one embodiment of the present invention, which is a part of a step of a method for manufacturing an amino acid sequence having a biantennary disialoglycoasparagine using erythropoietin as the model peptide. Specifically, it is a schematic diagram showing the step of deprotecting the protecting group of cysteine in fragment (A+B+C+D+E+F) having the amino acid sequence of amino acid sequences 1-166 of erythropoietin.

A 166-residue glycosylated polypeptide (23) having a disialo sugar chain on Asn at position 83 obtained in the above Step 8 (ca. 0.7 mg) was placed in an Eppendorf tube. After dissolving in 90% aqueous acetic acid solution (0.176 ml), silver acetate (ca. 0.8 mg) was added and reacted at room temperature with shading. After 3.5 hours, the production of the target object was confirmed with HPLC and ESI-MS. To the reaction solution was added dithiothreitol (6.0 mg), and after stirring at room temperature for 5 minutes, this was separated by centrifugation, and the supernatant excluding the precipitate was collected. The collected supernatant was filtered through a membrane filter, and the filtrate portion containing the target object was purified by HPLC [column: proteonavi (C4), φ 4.6×250 mm, flow rate: 1.0 mL/min, eluent solution A: 0.1% TFA-water solution B: 0.09% TFA/10% water/90% AN, gradient A:B=65:35->25:75(30 minutes) liner gradient] to afford a 166-residue glycosylated polypeptide (24) (SEQ ID NO:24) having Acm-groups-free at positions 7, 29, 33, and 161 and having a disialo dibenzyl sugar chain on Asn at position 83 (FIG. 11)

ESI-MS: m/z calcd. for $C_{895}H_{1448}N_{238}O_{299}S_5$: $[M+13H]^{13+}$ 1576.9, $[M+14H]^{14+}$ 1464.3, $[M+15H]^{15+}$ 1366.8, $[M+16H]^{16+}$ 1281.4, $[M+17H]^{17+}$ 1206.1, $[M+18H]^{18+}$ 1139.2, $[M+19H]^{19+}$ 1079.3, $[M+20H]^{20+}$ 1025.3, $[M+21H]^{21+}$ 976.6, $[M+22H]^{22+}$ 932.2, $[M+23H]^{23+}$ 891.7, $[M+24H]^{24+}$ 854.6, $[M+25H]^{25+}$ 820.5, $[M+26H]^{26+}$ 789.0, $[M+27H]^{27+}$ 759.8. found 1576.7, 1464.3, 1366.7, 1281.4, 1206.0, 1139.1, 1079.2, 1025.2, 976.5, 932.2, 891.6, 854.6, 820.4, 788.9, 759.8.

(III-10. Step 10: Folding Step)

Glycosylated polypeptide (24) having a disialo sugar chain on Asn at position 83 obtained in the above Step 9 was placed in a centrifuge tube. After dissolving in a buffer solution at pH 7.5 (13 ml) (prepared with 6 M guanidine hydrochloride solution and 0.1 mM tris-solution), this was left at room temperature. This solution was transferred to a dialysis membrane (Spectra/Pro, MWCO; 8000). This dialysis membrane was placed in outer dialysate A (prepared with 3 M guanidine hydrochloride solution, 0.1 mM tris-solution, 4 μM cysteine, and 0.5 μM cystine, pH 8.5), and dialyzed at 4° C. After 12 hours, this dialysis membrane was re-placed in outer dialysate B (prepared with 1 M guanidine hydrochloride solution, and 0.1 mM tris-solution, pH 8.0), and dialyzed at 4° C. After 8 hours, this dialysis membrane was re-placed in outer dialysate C (10 mM tris-solution, pH 7.0), and dialyzed at 4° C. After 24 hours, this dialysis membrane was taken out of the outer dialysate, and the solution inside the dialysis membrane was transferred to a centrifuge tube. The solution inside the dialysis membrane was directly purified by HPLC [column: proteonavi (C4), φ 4.6×250 mm, flow rate: 1.0 mL/min, eluent solution A: 0.1% TFA-water solution B: 0.09% TFA/10% water/90% AN, gradient A:B=60:40->25:75(30 minutes) liner gradient] to afford glycosylated polypeptide (25) (SEQ ID NO:25). The glycosylated polypeptide (25) after folding has a disulfide bond between cysteine at position 7 and cysteine at position 161, and a disulfide bond between cysteine at position 2'9 and cysteine at position 33.

ESI-MS: m/z calcd. for $C_{895}H_{1444}N_{238}O_{299}S_5$ $[M+11H]^{11+}$ 1863.1, $[M+12H]^{12+}$ 1707.9, $[M+13H]^{13+}$ 1576.6, $[M+14H]^{14+}$ 1464.1, $[M+15H]^{15+}$ 1366.5, $[M+16H]^{16+}$ 1281.2, $[M+17H]^{17+}$ 1205.9, $[M+18H]^{18+}$ 1138.9. found 1863.2, 1708.0, 1576.6, 1464.0, 1366.5, 1281.2, 1205.8, 1138.9.

The invention claimed is:

1. A method for manufacturing a glycopeptide having a sialyl sugar chain, characterized in that it comprises the following steps of:

(1) binding a resin having a hydroxyl group with an amino acid having the amino group nitrogen protected with a Boc group;
   wherein said binding step is a step of binding the hydroxyl group of said resin with the carboxyl group of said amino acid by an esterification reaction,
   (2) forming a free amino group by detaching said Boc group;
   (3) repeating at least once the following steps (i) and (ii) of:
      (i) elongating the amino acid bound to the resin by further binding another amino acid having the amino group nitrogen protected with a Boc group,
      wherein said elongation step is a step of binding the carboxyl group of said another amino acid with said free amino group of the amino acid bound to said resin,
      (ii) forming a free amino group by detaching said Boc group in (i); and
   (4) cleaving the resin with an acid;
   wherein said amino acid in step (1) and/or said another amino acid in at least one of (i) in step (3) is a glycosylated amino acid, said glycosylated amino acid has a sialic acid at at least one of the sugar chain non-reducing terminals, and the carboxyl group of said sialic acid is protected with a phenacyl group.

2. The manufacturing method according to claim 1, wherein said glycosylated amino acid is an asparagine-linked sugar chain or a mucin-linked sugar chain.

3. The manufacturing method according to claim 1, wherein said acid in said step (4) is a mixed acid of trifluoroacetic acid/trifluoromethanesulfonic acid/dimethyl sulfide/m-cresol.

4. The manufacturing method according to claim 1, wherein said amino acid in said step (1) and/or said another amino acid in at least one of (i) in said step (3) is a base-labile non-naturally occurring amino acid.

5. The manufacturing method according to claim 1, wherein at least one of said glycosylated amino acids is sialylglycoasparagine, and said sialylglycoasparagine has 6 or more sugar residues.

6. The manufacturing method according to claim 1, wherein at least one of said glycosylated amino acids is sialylglycoasparagine, and said sialylglycoasparagine has 9 to 11 sugar residues.

7. The manufacturing method according to claim 1, wherein at least one of said glycosylated amino acids is sialylglycoasparagine, and said glycoasparagine has 6 or more sugar residues and has a biantennary sugar chain bound thereto.

8. The manufacturing method according to claim 1, wherein said glycosylated amino acid is represented by the following Formula (1):

[Chemical Formula 1]

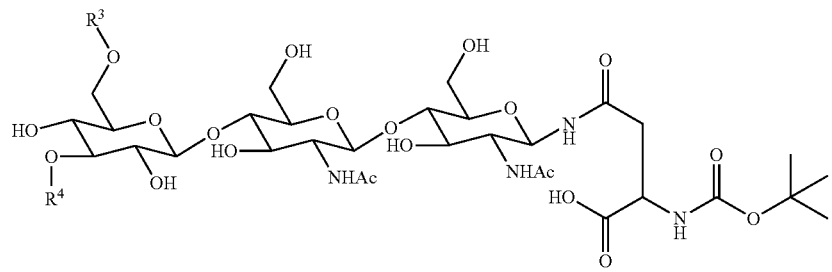

(1)

wherein one of $R^3$ and $R^4$ is the following Formula (2), and the other is a group selected from the group consisting of a hydrogen atom and groups shown in the following Formulae (2) to (6):

[Chemical Formula 2]

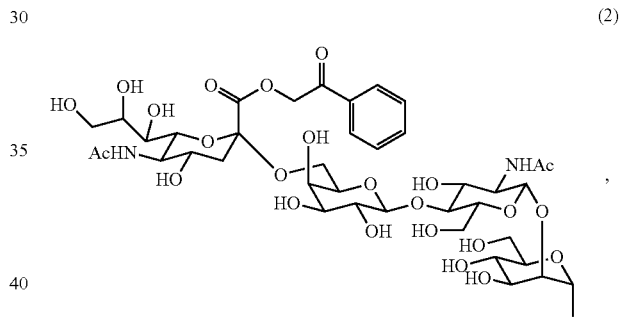

(2)

[Chemical Formula 3]

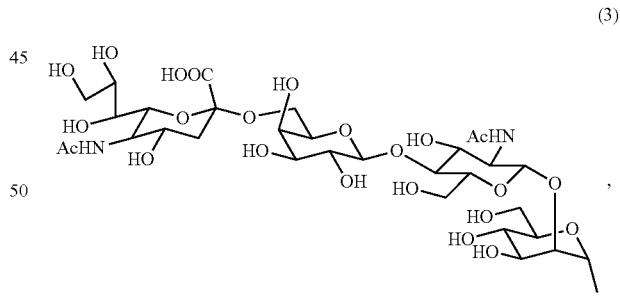

(3)

[Chemical Formula 4]

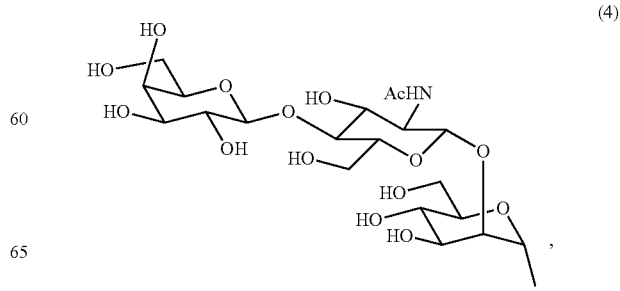

(4)

[Chemical Formula 5]

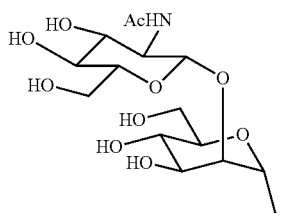
(5)

[Chemical Formula 6]

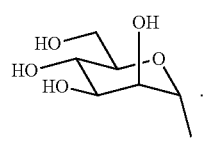
(6)

9. The manufacturing method according to claim 1, further comprising a step of binding a thiol compound to the resin before said step (1).

10. The manufacturing method according to claim 9, further comprising a step of (5) linking a thioester form of a glycopeptide having a sialyl sugar chain with a peptide or a glycopeptide fragment after said step (4).

11. The manufacturing method according to claim 1, further comprising a step of allowing a labeling agent to react before the cleaving of the resin with the acid in said step (4).

12. The manufacturing method according to claim 11, wherein the labeling agent is dansyl halide.

13. The manufacturing method according to claim 1, wherein at least one of the elongating and/or detaching steps of (2) to (3) further comprises heating with microwave irradiation.

14. The method for manufacturing a glycopeptide having a sialyl sugar chain according to claim 1, further comprising a step of deprotecting the phenacyl group protecting the carboxyl group of said sialic acid after said step (4).

15. A method for manufacturing a sialylglycoasparagine derivative in which the amino group of sialylglycoasparagine is protected with a Boc group and the carboxyl group of the sialic acid at the sugar chain non-reducing terminal is protected with a phenacyl group, comprising the steps of:
introducing a phenacyl group into a sialylglycoasparagine derivative having the amino group of the asparagine protected with a lipophilic protecting group,
detaching the lipophilic protecting group of the sialylglycoasparagine having a phenacyl group introduced, and
introducing a Boc group into the sialylglycoasparagine having the lipophilic protecting group detached.

16. The manufacturing method according to claim 15, wherein said lipophilic protecting group is Fmoc.

* * * * *

UNITED STATES PATENT AND TRADEMARK OFFICE
CERTIFICATE OF CORRECTION

PATENT NO. : 9,073,978 B2
APPLICATION NO. : 14/004122
DATED : July 7, 2015
INVENTOR(S) : Kajihara et al.

It is certified that error appears in the above-identified patent and that said Letters Patent is hereby corrected as shown below:

In the Specification:
Column 6, Line 33, [Chemical Formula 5]: Delete "-continued"

Column 13, Line 43, [Equation 1]: Please correct

" 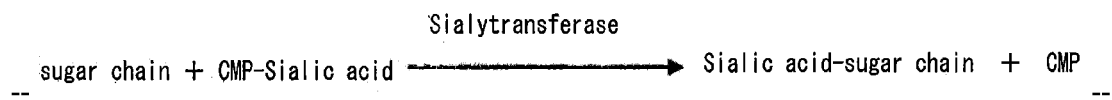

to read

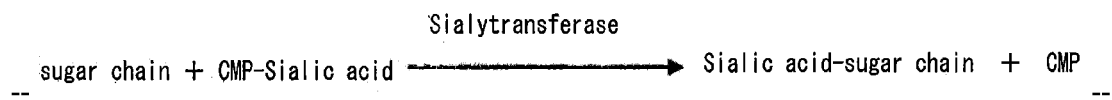
--  --

Column 14, Line 5: Please correct "ST6GalNAc-11" to read -- ST6GalNAc-II --

Column 29, Line 10: Please correct "Fragment (C+D'+"
   to read -- Fragment (C+D+ --

Column 32, Line 8: Please correct "[M+2E]$^{2+}$ 1677.5,"
   to read -- [M+2H]$^{2+}$ 1677.5, --

Column 35, Line 15: Please correct "ϕ 10×250 μm"
   to read -- ϕ 10×250 mm --

Column 36, Line 5: Please correct "890.8[M+18H] 841.3."
   to read -- 890.8, [M+18H]$^{18+}$ 841.3, --

Column 37, Line 8: Please correct "1385.7, [M+16H]$^{15+}$ 1229.2,"
   to read -- 1385.7, [M+16H]$^{16+}$ 1229.2, --

Signed and Sealed this
Seventeenth Day of May, 2016

Michelle K. Lee
*Director of the United States Patent and Trademark Office*

CERTIFICATE OF CORRECTION (continued)
U.S. Pat. No. 9,073,978 B2

Line 11: Please correct "904.1, $[M+24H]^{21+}$ 866.5,"
to read -- 904.1, $[M+24H]^{24+}$ 866.5, --

Column 38, Line 33: Please correct "position 2'9 and"
to read -- position 29 and --

SEQUENCE LISTING

<160> NUMBER OF SEQ ID NOS: 25

<210> SEQ ID NO 1
<211> LENGTH: 10
<212> TYPE: PRT
<213> ORGANISM: Artificial
<220> FEATURE:
<223> OTHER INFORMATION: Chemically synthesized
<220> FEATURE:
<221> NAME/KEY: CARBOHYD
<222> LOCATION: (2)..(2)
<223> OTHER INFORMATION: Diphenacyl disialooligosaccharide is added to
      Asn
<220> FEATURE:
<221> NAME/KEY: BINDING
<222> LOCATION: (10)..(10)
<223> OTHER INFORMATION: Sulphonic acid ethyl thioester

<400> SEQUENCE: 1

Thr Asn Tyr Ser Val Thr Asp Leu Asn Tyr
1               5                   10

<210> SEQ ID NO 2
<211> LENGTH: 10
<212> TYPE: PRT
<213> ORGANISM: Artificial

```
<220> FEATURE:
<223> OTHER INFORMATION: Chemically synthesized
<220> FEATURE:
<221> NAME/KEY: CARBOHYD
<222> LOCATION: (4)..(4)
<223> OTHER INFORMATION: Diphenacyl disialooligosaccharide is added to
      Asn
<220> FEATURE:
<221> NAME/KEY: BINDING
<222> LOCATION: (10)..(10)
<223> OTHER INFORMATION: Sulphonic acid ethyl thioester

<400> SEQUENCE: 2

Ser Leu Gln Asn Ala Ser Ala Ile Glu Ser
1               5                   10

<210> SEQ ID NO 3
<211> LENGTH: 21
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (2)..(2)
<223> OTHER INFORMATION: BOC
<220> FEATURE:
<221> NAME/KEY: BINDING
<222> LOCATION: (4)..(4)
<223> OTHER INFORMATION: OtBu
<220> FEATURE:
<221> NAME/KEY: BINDING
<222> LOCATION: (7)..(7)
<223> OTHER INFORMATION: tBu
<220> FEATURE:
<221> NAME/KEY: BINDING
<222> LOCATION: (8)..(8)
<223> OTHER INFORMATION: Pbf
<220> FEATURE:
<221> NAME/KEY: BINDING
<222> LOCATION: (9)..(9)
<223> OTHER INFORMATION: OtBu
<220> FEATURE:
<221> NAME/KEY: BINDING
<222> LOCATION: (12)..(12)
<223> OTHER INFORMATION: Pbf
<220> FEATURE:
<221> NAME/KEY: BINDING
<222> LOCATION: (13)..(13)
<223> OTHER INFORMATION: tBu
<220> FEATURE:
<221> NAME/KEY: BINDING
<222> LOCATION: (14)..(14)
<223> OTHER INFORMATION: OtBu
<220> FEATURE:
<221> NAME/KEY: BINDING
<222> LOCATION: (15)..(15)
<223> OTHER INFORMATION: Acm
<220> FEATURE:
<221> NAME/KEY: BINDING
<222> LOCATION: (18)..(18)
<223> OTHER INFORMATION: Pbf

<400> SEQUENCE: 3

Ala Lys Ala Glu Leu Leu Tyr Arg Glu Leu Val Arg Ser Asp Cys Ile
1               5                   10                  15

Leu Arg Pro Pro Ala
            20

<210> SEQ ID NO 4
<211> LENGTH: 21
<212> TYPE: PRT
<213> ORGANISM: Artificial
<220> FEATURE:
```

<223> OTHER INFORMATION: Chemically synthesized
<220> FEATURE:
<221> NAME/KEY: BINDING
<222> LOCATION: (7)..(7)
<223> OTHER INFORMATION: Acm
<220> FEATURE:
<221> NAME/KEY: BINDING
<222> LOCATION: (21)..(21)
<223> OTHER INFORMATION: -SPh

<400> SEQUENCE: 4

Ala Pro Pro Arg Leu Ile Cys Asp Ser Arg Val Leu Glu Arg Tyr Leu
1               5                   10                  15

Leu Glu Ala Lys Ala
            20

<210> SEQ ID NO 5
<211> LENGTH: 28
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: tBu
<220> FEATURE:
<221> NAME/KEY: BINDING
<222> LOCATION: (3)..(3)
<223> OTHER INFORMATION: Trt
<220> FEATURE:
<221> NAME/KEY: BINDING
<222> LOCATION: (5)..(5)
<223> OTHER INFORMATION: Boc
<220> FEATURE:
<221> NAME/KEY: BINDING
<222> LOCATION: (6)..(6)
<223> OTHER INFORMATION: tBu
<220> FEATURE:
<221> NAME/KEY: BINDING
<222> LOCATION: (7)..(7)
<223> OTHER INFORMATION: OtBu
<220> FEATURE:
<221> NAME/KEY: BINDING
<222> LOCATION: (10)..(10)
<223> OTHER INFORMATION: tBu
<220> FEATURE:
<221> NAME/KEY: BINDING
<222> LOCATION: (12)..(12)
<223> OTHER INFORMATION: Trt
<220> FEATURE:
<221> NAME/KEY: BINDING
<222> LOCATION: (13)..(13)
<223> OTHER INFORMATION: OtBu
<220> FEATURE:
<221> NAME/KEY: BINDING
<222> LOCATION: (14)..(14)
<223> OTHER INFORMATION: Trt
<220> FEATURE:
<221> NAME/KEY: BINDING
<222> LOCATION: (16)..(16)
<223> OTHER INFORMATION: tBu
<220> FEATURE:
<221> NAME/KEY: BINDING
<222> LOCATION: (17)..(17)
<223> OTHER INFORMATION: Acm
<220> FEATURE:
<221> NAME/KEY: BINDING
<222> LOCATION: (18)..(18)
<223> OTHER INFORMATION: Trt
<220> FEATURE:
<221> NAME/KEY: BINDING
<222> LOCATION: (19)..(19)
<223> OTHER INFORMATION: OtBu
<220> FEATURE:
<221> NAME/KEY: BINDING

```
<222> LOCATION: (21)..(21)
<223> OTHER INFORMATION: Acm
<220> FEATURE:
<221> NAME/KEY: BINDING
<222> LOCATION: (23)..(23)
<223> OTHER INFORMATION: tBu
<220> FEATURE:
<221> NAME/KEY: BINDING
<222> LOCATION: (24)..(24)
<223> OTHER INFORMATION: tBu
<220> FEATURE:
<221> NAME/KEY: BINDING
<222> LOCATION: (26)..(26)
<223> OTHER INFORMATION: Trt
<220> FEATURE:
<221> NAME/KEY: BINDING
<222> LOCATION: (27)..(27)
<223> OTHER INFORMATION: Trt
<220> FEATURE:
<221> NAME/KEY: BINDING
<222> LOCATION: (28)..(28)
<223> OTHER INFORMATION: Trt

<400> SEQUENCE: 5

Tyr Phe Asn Val Lys Thr Asp Pro Val Thr Ile Asn Glu Asn Leu Ser
1               5                   10                  15
Cys His Glu Ala Cys Gly Thr Thr Ile Asn Gln Cys
            20                  25

<210> SEQ ID NO 6
<211> LENGTH: 28
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (8)..(8)
<223> OTHER INFORMATION: Acm
<220> FEATURE:
<221> NAME/KEY: BINDING
<222> LOCATION: (12)..(12)
<223> OTHER INFORMATION: Acm
<220> FEATURE:
<221> NAME/KEY: BINDING
<222> LOCATION: (28)..(28)
<223> OTHER INFORMATION: -SBn

<400> SEQUENCE: 6

Cys Gln Asn Ile Thr Thr Gly Cys Ala Glu His Cys Ser Leu Asn Glu
1               5                   10                  15
Asn Ile Thr Val Pro Asp Thr Lys Val Asn Phe Tyr
            20                  25

<210> SEQ ID NO 7
<211> LENGTH: 29
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (3)..(3)
<223> OTHER INFORMATION: di-Z
<220> FEATURE:
<221> NAME/KEY: BINDING
<222> LOCATION: (7)..(7)
<223> OTHER INFORMATION: Bn
<220> FEATURE:
<221> NAME/KEY: BINDING
<222> LOCATION: (8)..(8)
<223> OTHER INFORMATION: Bn
<220> FEATURE:
```

```
<221> NAME/KEY: BINDING
<222> LOCATION: (15)..(15)
<223> OTHER INFORMATION: CHO
<220> FEATURE:
<221> NAME/KEY: BINDING
<222> LOCATION: (17)..(17)
<223> OTHER INFORMATION: Bn
<220> FEATURE:
<221> NAME/KEY: BINDING
<222> LOCATION: (24)..(24)
<223> OTHER INFORMATION: Bn
<220> FEATURE:
<221> NAME/KEY: BINDING
<222> LOCATION: (26)..(26)
<223> OTHER INFORMATION: di-Z
<220> FEATURE:
<221> NAME/KEY: BINDING
<222> LOCATION: (27)..(27)
<223> OTHER INFORMATION: Cl-Z
<220> FEATURE:
<221> NAME/KEY: BINDING
<222> LOCATION: (28)..(28)
<223> OTHER INFORMATION: CHO
<220> FEATURE:
<221> NAME/KEY: MISC_FEATURE
<222> LOCATION: (29)..(29)
<223> OTHER INFORMATION: Xaa is Thiazolidine-4-carboxylic acid

<400> SEQUENCE: 7

Ala Gly Arg Leu Val Ala Glu Ser Leu Leu Ala Leu Gly Gln Trp Val
1               5                   10                  15

Glu Val Ala Gln Gln Gly Val Glu Met Arg Lys Trp Xaa
            20                  25

<210> SEQ ID NO 8
<211> LENGTH: 29
<212> TYPE: PRT
<213> ORGANISM: Artificial
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa is Thiazolidine-4-carboxylic acid
<220> FEATURE:
<221> NAME/KEY: BINDING
<222> LOCATION: (29)..(29)
<223> OTHER INFORMATION: Sulphonic acid ethyl thioester

<400> SEQUENCE: 8

Xaa Trp Lys Arg Met Glu Val Gly Gln Gln Ala Val Glu Val Trp Gln
1               5                   10                  15

Gly Leu Ala Leu Leu Ser Glu Ala Val Leu Arg Gly Ala
            20                  25

<210> SEQ ID NO 9
<211> LENGTH: 14
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Cl-Z
<220> FEATURE:
<221> NAME/KEY: BINDING
<222> LOCATION: (2)..(2)
<223> OTHER INFORMATION: Bn
<220> FEATURE:
<221> NAME/KEY: BINDING
<222> LOCATION: (4)..(4)
<223> OTHER INFORMATION: DNP
```

```
<220> FEATURE:
<221> NAME/KEY: BINDING
<222> LOCATION: (9)..(9)
<223> OTHER INFORMATION: Bn
<220> FEATURE:
<221> NAME/KEY: BINDING
<222> LOCATION: (10)..(10)
<223> OTHER INFORMATION: CHO
<220> FEATURE:
<221> NAME/KEY: BINDING
<222> LOCATION: (13)..(13)
<223> OTHER INFORMATION: Bn
<220> FEATURE:
<221> NAME/KEY: BINDING
<222> LOCATION: (14)..(14)
<223> OTHER INFORMATION: Bn

<400> SEQUENCE: 9

Lys Asp Val His Leu Gln Leu Pro Glu Trp Pro Gln Ser Ser
1               5                   10

<210> SEQ ID NO 10
<211> LENGTH: 19
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Cl-Z
<220> FEATURE:
<221> NAME/KEY: BINDING
<222> LOCATION: (2)..(2)
<223> OTHER INFORMATION: Bn
<220> FEATURE:
<221> NAME/KEY: BINDING
<222> LOCATION: (4)..(4)
<223> OTHER INFORMATION: DNP
<220> FEATURE:
<221> NAME/KEY: BINDING
<222> LOCATION: (9)..(9)
<223> OTHER INFORMATION: Bn
<220> FEATURE:
<221> NAME/KEY: BINDING
<222> LOCATION: (10)..(10)
<223> OTHER INFORMATION: CHO
<220> FEATURE:
<221> NAME/KEY: BINDING
<222> LOCATION: (13)..(13)
<223> OTHER INFORMATION: Bn
<220> FEATURE:
<221> NAME/KEY: BINDING
<222> LOCATION: (14)..(14)
<223> OTHER INFORMATION: Bn
<220> FEATURE:
<221> NAME/KEY: BINDING
<222> LOCATION: (15)..(15)
<223> OTHER INFORMATION: Diphenylacyl-disialo sugar chain added to Asn
<220> FEATURE:
<221> NAME/KEY: MISC_FEATURE
<222> LOCATION: (19)..(19)
<223> OTHER INFORMATION: Xaa is Thiazolidine-4-carboxylic acid

<400> SEQUENCE: 10

Lys Asp Val His Leu Gln Leu Pro Glu Trp Pro Gln Ser Ser Asn Val
1               5                   10                  15

Leu Leu Xaa

<210> SEQ ID NO 11
<211> LENGTH: 19
<212> TYPE: PRT
<213> ORGANISM: Artificial
<220> FEATURE:
```

<223> OTHER INFORMATION: Chemically synthesized
<220> FEATURE:
<221> NAME/KEY: MISC_FEATURE
<222> LOCATION: (1)..(1)
<223> OTHER INFORMATION: Xaa is Thiazolidine-4-carboxylic acid
<220> FEATURE:
<221> NAME/KEY: BINDING
<222> LOCATION: (5)..(5)
<223> OTHER INFORMATION: Diphenylacyl-sialo sugar chain added to Asn
<220> FEATURE:
<221> NAME/KEY: BINDING
<222> LOCATION: (10)..(10)
<223> OTHER INFORMATION: CHO
<220> FEATURE:
<221> NAME/KEY: BINDING
<222> LOCATION: (19)..(19)
<223> OTHER INFORMATION: Sulphonic acid ethyl thioester

<400> SEQUENCE: 11

Xaa Leu Leu Val Asn Ser Ser Gln Pro Trp Glu Pro Leu Gln Leu His
1               5                   10                  15

Val Asp Lys

<210> SEQ ID NO 12
<211> LENGTH: 30
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (2)..(2)
<223> OTHER INFORMATION: Bn
<220> FEATURE:
<221> NAME/KEY: BINDING
<222> LOCATION: (5)..(5)
<223> OTHER INFORMATION: Bn
<220> FEATURE:
<221> NAME/KEY: BINDING
<222> LOCATION: (8)..(8)
<223> OTHER INFORMATION: Bn
<220> FEATURE:
<221> NAME/KEY: BINDING
<222> LOCATION: (11)..(11)
<223> OTHER INFORMATION: Bn
<220> FEATURE:
<221> NAME/KEY: BINDING
<222> LOCATION: (12)..(12)
<223> OTHER INFORMATION: Cl-Z
<220> FEATURE:
<221> NAME/KEY: BINDING
<222> LOCATION: (13)..(13)
<223> OTHER INFORMATION: Bn
<220> FEATURE:
<221> NAME/KEY: BINDING
<222> LOCATION: (18)..(18)
<223> OTHER INFORMATION: Di-Z
<220> FEATURE:
<221> NAME/KEY: BINDING
<222> LOCATION: (21)..(21)
<223> OTHER INFORMATION: Bn
<220> FEATURE:
<221> NAME/KEY: BINDING
<222> LOCATION: (22)..(22)
<223> OTHER INFORMATION: Bn
<220> FEATURE:
<221> NAME/KEY: BINDING
<222> LOCATION: (24)..(24)
<223> OTHER INFORMATION: Bn
<220> FEATURE:
<221> NAME/KEY: BINDING
<222> LOCATION: (25)..(25)
<223> OTHER INFORMATION: di-Z
<220> FEATURE:
<221> NAME/KEY: BINDING
<222> LOCATION: (28)..(28)

```
<223> OTHER INFORMATION: Bn
<220> FEATURE:
<221> NAME/KEY: MISC_FEATURE
<222> LOCATION: (30)..(30)
<223> OTHER INFORMATION: Xaa is Thiazolidine-4-carboxylic acid

<400> SEQUENCE: 12

Ala Ser Ala Ala Asp Pro Pro Ser Ile Ala Glu Lys Glu Ala Gly Leu
1               5                   10                  15

Ala Arg Leu Leu Thr Thr Leu Ser Arg Leu Gly Ser Val Xaa
            20                  25                  30

<210> SEQ ID NO 13
<211> LENGTH: 30
<212> TYPE: PRT
<213> ORGANISM: Artificial
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa is Thiazolidine-4-carboxylic acid
<220> FEATURE:
<221> NAME/KEY: BINDING
<222> LOCATION: (30)..(30)
<223> OTHER INFORMATION: Sulphonic acid ethyl thioester

<400> SEQUENCE: 13

Xaa Val Ser Gly Leu Arg Ser Leu Thr Thr Leu Leu Arg Ala Leu Gly
1               5                   10                  15

Ala Glu Lys Glu Ala Ile Ser Pro Pro Asp Ala Ala Ser Ala
            20                  25                  30

<210> SEQ ID NO 14
<211> LENGTH: 39
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: PbF
<220> FEATURE:
<221> NAME/KEY: BINDING
<222> LOCATION: (2)..(2)
<223> OTHER INFORMATION: OtBu
<220> FEATURE:
<221> NAME/KEY: BINDING
<222> LOCATION: (4)..(4)
<223> OTHER INFORMATION: tBu
<220> FEATURE:
<221> NAME/KEY: BINDING
<222> LOCATION: (5)..(5)
<223> OTHER INFORMATION: Pbf
<220> FEATURE:
<221> NAME/KEY: BINDING
<222> LOCATION: (6)..(6)
<223> OTHER INFORMATION: Acm
<220> FEATURE:
<221> NAME/KEY: BINDING
<222> LOCATION: (8)..(8)
<223> OTHER INFORMATION: OtBu
<220> FEATURE:
<221> NAME/KEY: BINDING
<222> LOCATION: (10)..(10)
<223> OTHER INFORMATION: tBu
<220> FEATURE:
<221> NAME/KEY: BINDING
<222> LOCATION: (11)..(11)
<223> OTHER INFORMATION: tBu
<220> FEATURE:
<221> NAME/KEY: BINDING
```

```
<222> LOCATION: (13)..(13)
<223> OTHER INFORMATION: Boc
<220> FEATURE:
<221> NAME/KEY: BINDING
<222> LOCATION: (15)..(15)
<223> OTHER INFORMATION: Boc
<220> FEATURE:
<221> NAME/KEY: BINDING
<222> LOCATION: (17)..(17)
<223> OTHER INFORMATION: Pbf
<220> FEATURE:
<221> NAME/KEY: BINDING
<222> LOCATION: (20)..(20)
<223> OTHER INFORMATION: Trt
<220> FEATURE:
<221> NAME/KEY: BINDING
<222> LOCATION: (21)..(21)
<223> OTHER INFORMATION: tBu
<220> FEATURE:
<221> NAME/KEY: BINDING
<222> LOCATION: (22)..(22)
<223> OTHER INFORMATION: tBu
<220> FEATURE:
<221> NAME/KEY: BINDING
<222> LOCATION: (24)..(24)
<223> OTHER INFORMATION: Pbf
<220> FEATURE:
<221> NAME/KEY: BINDING
<222> LOCATION: (27)..(27)
<223> OTHER INFORMATION: Boc
<220> FEATURE:
<221> NAME/KEY: BINDING
<222> LOCATION: (28)..(28)
<223> OTHER INFORMATION: Pbf
<220> FEATURE:
<221> NAME/KEY: BINDING
<222> LOCATION: (30)..(30)
<223> OTHER INFORMATION: tBu
<220> FEATURE:
<221> NAME/KEY: BINDING
<222> LOCATION: (31)..(31)
<223> OTHER INFORMATION: OtBu
<220> FEATURE:
<221> NAME/KEY: BINDING
<222> LOCATION: (33)..(33)
<223> OTHER INFORMATION: tBu
<220> FEATURE:
<221> NAME/KEY: BINDING
<222> LOCATION: (35)..(35)
<223> OTHER INFORMATION: tBu
<220> FEATURE:
<221> NAME/KEY: BINDING
<222> LOCATION: (36)..(36)
<223> OTHER INFORMATION: Pbf
<220> FEATURE:
<221> NAME/KEY: BINDING
<222> LOCATION: (39)..(39)
<223> OTHER INFORMATION: Trt

<400> SEQUENCE: 14

Arg Asp Gly Thr Arg Cys Ala Glu Gly Thr Tyr Leu Lys Leu Lys Gly
1               5                   10                  15

Arg Leu Phe Asn Ser Tyr Val Arg Phe Leu Lys Arg Phe Thr Asp Ala
            20                  25                  30

Thr Ile Thr Arg Leu Pro Cys
        35

<210> SEQ ID NO 15
<211> LENGTH: 39
<212> TYPE: PRT
<213> ORGANISM: Artificial
<220> FEATURE:
<223> OTHER INFORMATION: Chemically synthesized
<220> FEATURE:
<221> NAME/KEY: BINDING
```

```
<222> LOCATION: (34)..(34)
<223> OTHER INFORMATION: Acm

<400> SEQUENCE: 15

Cys Pro Leu Arg Thr Ile Thr Ala Asp Thr Phe Arg Lys Leu Phe Arg
1               5                   10                  15

Val Tyr Ser Asn Phe Leu Arg Gly Lys Leu Lys Leu Tyr Thr Gly Glu
            20                  25                  30

Ala Cys Arg Thr Gly Asp Arg
        35

<210> SEQ ID NO 16
<211> LENGTH: 69
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (64)..(64)
<223> OTHER INFORMATION: Acm

<400> SEQUENCE: 16

Cys Val Ser Gly Leu Arg Ser Leu Thr Thr Leu Leu Arg Ala Leu Gly
1               5                   10                  15

Ala Glu Lys Glu Ala Ile Ser Pro Pro Asp Ala Ala Ser Ala Cys Pro
            20                  25                  30

Leu Arg Thr Ile Thr Ala Asp Thr Phe Arg Lys Leu Phe Arg Val Tyr
        35                  40                  45

Ser Asn Phe Leu Arg Gly Lys Leu Lys Leu Tyr Thr Gly Glu Ala Cys
    50                  55                  60

Arg Thr Gly Asp Arg
65

<210> SEQ ID NO 17
<211> LENGTH: 88
<212> TYPE: PRT
<213> ORGANISM: Artificial
<220> FEATURE:
<223> OTHER INFORMATION: Chemically synthesized
<220> FEATURE:
<221> NAME/KEY: CARBOHYD
<222> LOCATION: (5)..(5)
<223> OTHER INFORMATION: Disialooligosaccharide is added to Asn
<220> FEATURE:
<221> NAME/KEY: BINDING
<222> LOCATION: (83)..(83)
<223> OTHER INFORMATION: Acm

<400> SEQUENCE: 17

Cys Leu Leu Val Asn Ser Ser Gln Pro Trp Glu Pro Leu Gln Leu His
1               5                   10                  15

Val Asp Lys Cys Val Ser Gly Leu Arg Ser Leu Thr Thr Leu Leu Arg
            20                  25                  30

Ala Leu Gly Ala Glu Lys Glu Ala Ile Ser Pro Pro Asp Ala Ala Ser
        35                  40                  45

Ala Cys Pro Leu Arg Thr Ile Thr Ala Asp Thr Phe Arg Lys Leu Phe
    50                  55                  60

Arg Val Tyr Ser Asn Phe Leu Arg Gly Lys Leu Lys Leu Tyr Thr Gly
65                  70                  75                  80

Glu Ala Cys Arg Thr Gly Asp Arg
            85
```

```
<210> SEQ ID NO 18
<211> LENGTH: 117
<212> TYPE: PRT
<213> ORGANISM: Artificial
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 1C has Thiazolidine ring
<220> FEATURE:
<221> NAME/KEY: CARBOHYD
<222> LOCATION: (33)..(33)
<223> OTHER INFORMATION: Disialooligosaccharide is added to Asn
<220> FEATURE:
<221> NAME/KEY: BINDING
<222> LOCATION: (112)..(112)
<223> OTHER INFORMATION: Acm

<400> SEQUENCE: 18

Cys Trp Lys Arg Met Glu Val Gly Gln Gln Ala Val Glu Val Trp Gln
1               5                   10                  15

Gly Leu Ala Leu Leu Ser Glu Ala Val Leu Arg Gly Ala Cys Leu Leu
            20                  25                  30

Val Asn Ser Ser Gln Pro Trp Glu Pro Leu Gln Leu His Val Asp Lys
        35                  40                  45

Cys Val Ser Gly Leu Arg Ser Leu Thr Thr Leu Leu Arg Ala Leu Gly
    50                  55                  60

Ala Glu Lys Glu Ala Ile Ser Pro Pro Asp Ala Ala Ser Ala Cys Pro
65                  70                  75                  80

Leu Arg Thr Ile Thr Ala Asp Thr Phe Arg Lys Leu Phe Arg Val Tyr
                85                  90                  95

Ser Asn Phe Leu Arg Gly Lys Leu Lys Leu Tyr Thr Gly Glu Ala Cys
            100                 105                 110

Arg Thr Gly Asp Arg
        115

<210> SEQ ID NO 19
<211> LENGTH: 117
<212> TYPE: PRT
<213> ORGANISM: Artificial
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: 1C has Thiazolidine ring
<220> FEATURE:
<221> NAME/KEY: CARBOHYD
<222> LOCATION: (33)..(33)
<223> OTHER INFORMATION: Disialooligosaccharide is added to Asn
<220> FEATURE:
<221> NAME/KEY: BINDING
<222> LOCATION: (112)..(112)
<223> OTHER INFORMATION: Acm

<400> SEQUENCE: 19

Cys Trp Lys Arg Met Glu Val Gly Gln Gln Ala Val Glu Val Trp Gln
1               5                   10                  15

Gly Leu Ala Leu Leu Ser Glu Ala Val Leu Arg Gly Ala Ala Leu Leu
            20                  25                  30

Val Asn Ser Ser Gln Pro Trp Glu Pro Leu Gln Leu His Val Asp Lys
        35                  40                  45

Ala Val Ser Gly Leu Arg Ser Leu Thr Thr Leu Leu Arg Ala Leu Gly
    50                  55                  60
```

```
Ala Glu Lys Glu Ala Ile Ser Pro Pro Asp Ala Ala Ser Ala Ala Pro
 65                  70                  75                  80

Leu Arg Thr Ile Thr Ala Asp Thr Phe Arg Lys Leu Phe Arg Val Tyr
                 85                  90                  95

Ser Asn Phe Leu Arg Gly Lys Leu Lys Leu Tyr Thr Gly Glu Ala Cys
             100                 105                 110

Arg Thr Gly Asp Arg
        115

<210> SEQ ID NO 20
<211> LENGTH: 117
<212> TYPE: PRT
<213> ORGANISM: Artificial
<220> FEATURE:
<223> OTHER INFORMATION: Chemically synthesized
<220> FEATURE:
<221> NAME/KEY: CARBOHYD
<222> LOCATION: (33)..(33)
<223> OTHER INFORMATION: Disialooligosaccharide is added to Asn
<220> FEATURE:
<221> NAME/KEY: BINDING
<222> LOCATION: (112)..(112)
<223> OTHER INFORMATION: Acm

<400> SEQUENCE: 20

Cys Trp Lys Arg Met Glu Val Gly Gln Gln Ala Val Glu Val Trp Gln
 1               5                  10                  15

Gly Leu Ala Leu Leu Ser Glu Ala Val Leu Arg Gly Ala Ala Leu Leu
                 20                  25                  30

Val Asn Ser Ser Gln Pro Trp Glu Pro Leu Gln Leu His Val Asp Lys
             35                  40                  45

Ala Val Ser Gly Leu Arg Ser Leu Thr Thr Leu Leu Arg Ala Leu Gly
 50                  55                  60

Ala Glu Lys Glu Ala Ile Ser Pro Pro Asp Ala Ala Ser Ala Ala Pro
 65                  70                  75                  80

Leu Arg Thr Ile Thr Ala Asp Thr Phe Arg Lys Leu Phe Arg Val Tyr
                 85                  90                  95

Ser Asn Phe Leu Arg Gly Lys Leu Lys Leu Tyr Thr Gly Glu Ala Cys
             100                 105                 110

Arg Thr Gly Asp Arg
        115

<210> SEQ ID NO 21
<211> LENGTH: 49
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (7)..(7)
<223> OTHER INFORMATION: Acm
<220> FEATURE:
<221> NAME/KEY: BINDING
<222> LOCATION: (29)..(29)
<223> OTHER INFORMATION: Acm
<220> FEATURE:
<221> NAME/KEY: BINDING
<222> LOCATION: (33)..(33)
<223> OTHER INFORMATION: Acm
<220> FEATURE:
<221> NAME/KEY: BINDING
<222> LOCATION: (49)..(49)
<223> OTHER INFORMATION: -Sulphonic acid ethyl thioester
```

-continued

```
<400> SEQUENCE: 21

Ala Pro Pro Arg Leu Ile Cys Asp Ser Arg Val Leu Glu Arg Tyr Leu
1               5                   10                  15

Leu Glu Ala Lys Ala Cys Gln Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr

<210> SEQ ID NO 22
<211> LENGTH: 166
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (7)..(7)
<223> OTHER INFORMATION: Acm
<220> FEATURE:
<221> NAME/KEY: BINDING
<222> LOCATION: (29)..(29)
<223> OTHER INFORMATION: Acm
<220> FEATURE:
<221> NAME/KEY: BINDING
<222> LOCATION: (33)..(33)
<223> OTHER INFORMATION: Acm
<220> FEATURE:
<221> NAME/KEY: CARBOHYD
<222> LOCATION: (83)..(83)
<223> OTHER INFORMATION: Disialooligosaccharide is added to Asn
<220> FEATURE:
<221> NAME/KEY: BINDING
<222> LOCATION: (161)..(161)
<223> OTHER INFORMATION: Acm

<400> SEQUENCE: 22

Ala Pro Pro Arg Leu Ile Cys Asp Ser Arg Val Leu Glu Arg Tyr Leu
1               5                   10                  15

Leu Glu Ala Lys Ala Cys Gln Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Cys Trp Lys Arg Met Glu Val Gly Gln Gln Ala Val Glu Val Trp
    50                  55                  60

Gln Gly Leu Ala Leu Leu Ser Glu Ala Val Leu Arg Gly Ala Cys Leu
65              70                  75                  80

Leu Val Asn Ser Ser Gln Pro Trp Glu Pro Leu Gln Leu His Val Asp
                85                  90                  95

Lys Cys Val Ser Gly Leu Arg Ser Leu Thr Thr Leu Leu Arg Ala Leu
            100                 105                 110

Gly Ala Glu Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 23
<211> LENGTH: 166
```

<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (7)..(7)
<223> OTHER INFORMATION: Acm
<220> FEATURE:
<221> NAME/KEY: BINDING
<222> LOCATION: (29)..(29)
<223> OTHER INFORMATION: Acm
<220> FEATURE:
<221> NAME/KEY: BINDING
<222> LOCATION: (33)..(33)
<223> OTHER INFORMATION: Acm
<220> FEATURE:
<221> NAME/KEY: CARBOHYD
<222> LOCATION: (83)..(83)
<223> OTHER INFORMATION: Disialooligosaccharide is added to Asn
<220> FEATURE:
<221> NAME/KEY: BINDING
<222> LOCATION: (161)..(161)
<223> OTHER INFORMATION: Acm

<400> SEQUENCE: 23

Ala Pro Pro Arg Leu Ile Cys Asp Ser Arg Val Leu Glu Arg Tyr Leu
1               5                   10                  15

Leu Glu Ala Lys Ala Ala Gln Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Ala Ala Leu
65                  70                  75                  80

Leu Val Asn Ser Ser Gln Pro Trp Glu Pro Leu Gln Leu His Val Asp
                85                  90                  95

Lys Cys Val Ser Gly Leu Arg Ser Leu Thr Thr Leu Leu Arg Ala Leu
            100                 105                 110

Gly Ala Glu Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 24
<211> LENGTH: 166
<212> TYPE: PRT
<213> ORGANISM: Artificial
<220> FEATURE:
<223> OTHER INFORMATION: Chemically synthesized
<220> FEATURE:
<221> NAME/KEY: CARBOHYD
<222> LOCATION: (83)..(83)
<223> OTHER INFORMATION: Disialooligosaccharide is added to Asn

<400> SEQUENCE: 24

Ala Pro Pro Arg Leu Ile Cys Asp Ser Arg Val Leu Glu Arg Tyr Leu
1               5                   10                  15

Leu Glu Ala Lys Ala Ala Gln Asn Ile Thr Thr Gly Cys Ala Glu His
                20                  25                  30

```
Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Ala Ala Leu
 65                  70                  75                  80

Leu Val Asn Ser Ser Gln Pro Trp Glu Pro Leu Gln Leu His Val Asp
                    85                  90                  95

Lys Cys Val Ser Gly Leu Arg Ser Leu Thr Thr Leu Leu Arg Ala Leu
            100                 105                 110

Gly Ala Glu Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165
```

<210> SEQ ID NO 25
<211> LENGTH: 166
<212> TYPE: PRT
<213> ORGANISM: Artificial
<220> FEATURE:
<223> OTHER INFORMATION: Chemically synthesized
<220> FEATURE:
<221> NAME/KEY: DISULFID
<222> LOCATION: (7)..(161)
<220> FEATURE:
<221> NAME/KEY: DISULFID
<222> LOCATION: (29)..(33)

<400> SEQUENCE: 25

```
Ala Pro Pro Arg Leu Ile Cys Asp Ser Arg Val Leu Glu Arg Tyr Leu
 1               5                  10                  15

Leu Glu Ala Lys Ala Ala Gln Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Ala Ala Leu
 65                  70                  75                  80

Leu Val Asn Ser Ser Gln Pro Trp Glu Pro Leu Gln Leu His Val Asp
                    85                  90                  95

Lys Ala Val Ser Gly Leu Arg Ser Leu Thr Thr Leu Leu Arg Ala Leu
            100                 105                 110

Gly Ala Glu Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165
```